United States Patent
Hollman et al.

(10) Patent No.: US 8,486,189 B2
(45) Date of Patent: Jul. 16, 2013

(54) COSMETIC COMPRISING MULTI-COLORED LUSTROUS PEARLESCENT PIGMENTS

(75) Inventors: Aaron M. Hollman, Union, KY (US); Stephane Nicolas, Fleurines (FR); Philippe Schottland, West Chester, OH (US); Marguerite Debacker, Court Saint Etienne (BE); Aurelie Antonowicz, Gembioux (BE); Hai Hui Lin, Mason, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 13/524,052

(22) Filed: Jun. 15, 2012

(65) Prior Publication Data

US 2012/0251606 A1 Oct. 4, 2012

Related U.S. Application Data

(60) Division of application No. 11/931,658, filed on Oct. 31, 2007, now Pat. No. 8,221,536, which is a continuation-in-part of application No. 11/765,614, filed on Jun. 20, 2007, now Pat. No. 7,850,775.

(60) Provisional application No. 60/865,042, filed on Nov. 9, 2006.

(51) Int. Cl.
- *C09C 1/24* (2006.01)
- *C01G 49/06* (2006.01)
- *C01G 49/08* (2006.01)
- *C09C 1/15* (2006.01)

(52) U.S. Cl.
USPC .......................................... 106/456; 106/418

(58) Field of Classification Search
USPC ............... 106/415, 418, 439, 456; 252/63.56, 252/62.56; 148/105
See application file for complete search history.

(56) References Cited

U.S. PATENT DOCUMENTS

| | | | |
|---|---|---|---|
| 2,694,622 A | 11/1954 | Reed et al. |
| 3,087,829 A | 4/1963 | Linton |
| 3,874,890 A | 4/1975 | Bernhard et al. |
| 3,926,659 A | 12/1975 | Bernhard et al. |
| 3,931,025 A | 1/1976 | Woditsch et al. |
| 4,017,303 A | 4/1977 | Koester et al. |

(Continued)

FOREIGN PATENT DOCUMENTS

| | | |
|---|---|---|
| CN | 1856650 | 11/2006 |
| DE | 22 15 191 | 10/1972 |

(Continued)

OTHER PUBLICATIONS

Hua et al. "Influence of Au Loading on the Structure and catalytic performance of Au/ α-Fe2O3 Catalysts for low-temperature water-gas shift reaction", Journal of Fuel Chemistry and Technology, vol. 31, No. 6, Dec. 2003, pp. 558-563.

(Continued)

*Primary Examiner* — Pegah Parvini
(74) *Attorney, Agent, or Firm* — Frost Brown Todd LLC

(57) ABSTRACT

A cosmetic containing a pearlescent pigment comprising a substrate and a first layer, wherein the first layer comprises iron oxide, wherein the iron has from about 1% to about 30% Fe(II) and from about 70% to about 99% Fe(III).

4 Claims, 2 Drawing Sheets

Absorbance measurements of the filtrate solution for each red pearlescent pigment analyzed for acid resistance.

U.S. PATENT DOCUMENTS

| | | | |
|---|---|---|---|
| 4,146,403 A | 3/1979 | Armanini et al. | |
| 4,325,741 A * | 4/1982 | Otoi et al. | 106/419 |
| 4,435,220 A | 3/1984 | Watanabe et al. | |
| 4,606,914 A | 8/1986 | Miyoshi | |
| 4,622,074 A | 11/1986 | Miyoshi et al. | |
| 4,701,221 A | 10/1987 | Brunn et al. | |
| 4,702,775 A | 10/1987 | Ostertag | |
| 4,744,832 A | 5/1988 | Franz | |
| 4,838,648 A | 6/1989 | Phillips et al. | |
| 4,867,793 A | 9/1989 | Franz | |
| 4,948,631 A | 8/1990 | Ostertag et al. | |
| 4,992,262 A * | 2/1991 | Nakagaki et al. | 424/63 |
| 5,009,711 A | 4/1991 | Emmert | |
| 5,085,706 A | 2/1992 | Kuske | |
| 5,164,005 A | 11/1992 | Kuske et al. | |
| 5,208,081 A | 5/1993 | Gubitz et al. | |
| 5,223,360 A | 6/1993 | Prengel et al. | |
| 5,273,576 A | 12/1993 | Sullivan | |
| 5,277,711 A | 1/1994 | Schmidt | |
| 5,326,392 A | 7/1994 | Miller et al. | |
| 5,356,471 A | 10/1994 | Reynders | |
| 5,364,467 A | 11/1994 | Schmid | |
| 5,368,639 A | 11/1994 | Hasegawa et al. | |
| 5,374,306 A | 12/1994 | Schlegel | |
| 5,449,403 A | 9/1995 | Andrean et al. | |
| 5,472,491 A | 12/1995 | Duschek et al. | |
| 5,486,354 A | 1/1996 | Defossez et al. | |
| 5,486,631 A | 1/1996 | Mitchnick et al. | |
| 5,571,851 A | 11/1996 | Freeman et al. | |
| 5,582,817 A | 12/1996 | Otsu et al. | |
| 5,624,487 A | 4/1997 | Schmidt | |
| 5,695,747 A | 12/1997 | Forestier et al. | |
| 5,718,754 A | 2/1998 | MacPherson et al. | |
| 5,733,658 A | 3/1998 | Schmid et al. | |
| 5,738,717 A | 4/1998 | Oulsnam et al. | |
| 5,753,371 A | 5/1998 | Sullivan | |
| 5,759,255 A | 6/1998 | Venturini et al. | |
| 5,932,197 A | 8/1999 | Arnaud | |
| 5,958,125 A | 9/1999 | Schmid | |
| 5,958,197 A | 9/1999 | Allen et al. | |
| 6,019,831 A | 2/2000 | Schmidt et al. | |
| 6,086,846 A | 7/2000 | Burow et al. | |
| 6,132,873 A | 10/2000 | Dietz et al. | |
| 6,139,614 A | 10/2000 | Schmid et al. | |
| 6,139,615 A | 10/2000 | Jones | |
| 6,190,445 B1 | 2/2001 | Noguchi | |
| 6,235,185 B1 * | 5/2001 | Tanaka et al. | 205/508 |
| 6,280,714 B1 | 8/2001 | Arnaud et al. | |
| 6,290,766 B1 | 9/2001 | DeLuca, Jr. | |
| 6,372,517 B1 | 4/2002 | Lange | |
| 6,416,573 B2 | 7/2002 | Horino et al. | |
| 6,428,773 B1 | 8/2002 | Oko et al. | |
| 6,451,294 B1 | 9/2002 | Simon | |
| 6,485,556 B1 | 11/2002 | DeLuca, Jr. | |
| 6,488,758 B2 | 12/2002 | Glausch et al. | |
| 6,541,032 B1 | 4/2003 | Medelnick et al. | |
| 6,589,331 B2 | 7/2003 | Ostertag et al. | |
| 6,616,745 B1 | 9/2003 | Navarti et al. | |
| 6,620,233 B1 | 9/2003 | Seeger et al. | |
| 6,630,018 B2 | 10/2003 | Bauer et al. | |
| 6,632,275 B1 | 10/2003 | Schoen et al. | |
| 6,638,618 B2 | 10/2003 | Hayashi et al. | |
| 6,645,286 B2 | 11/2003 | Ostertag et al. | |
| 6,663,852 B2 | 12/2003 | Simon | |
| 6,689,205 B1 | 2/2004 | Bruckner et al. | |
| 6,689,206 B2 | 2/2004 | Meisen | |
| 6,692,561 B1 | 2/2004 | Schoen | |
| 6,719,837 B2 | 4/2004 | Bertaux | |
| 6,719,838 B2 | 4/2004 | Heider et al. | |
| 6,743,285 B1 * | 6/2004 | Anselmann et al. | 106/415 |
| 6,759,097 B2 | 7/2004 | Phillips et al. | |
| 6,773,499 B2 | 8/2004 | Schoen et al. | |
| 6,781,022 B1 | 8/2004 | Katrib et al. | |
| 6,790,452 B2 | 9/2004 | Kishida et al. | |
| 6,818,299 B2 | 11/2004 | Phillips et al. | |
| 6,838,166 B2 | 1/2005 | Phillips et al. | |
| 6,875,264 B2 | 4/2005 | Zimmermann et al. | |
| 6,884,289 B2 | 4/2005 | Schoen | |
| 6,902,609 B2 | 6/2005 | Steffenino et al. | |
| 6,902,807 B1 | 6/2005 | Argoitia et al. | |
| 7,014,700 B2 | 3/2006 | DeLuca, Jr. et al. | |
| 7,019,048 B2 | 3/2006 | Brehm | |
| 7,122,245 B2 | 10/2006 | Morton-Finger | |
| 7,169,735 B2 | 1/2007 | Sagae | |
| 7,189,454 B2 | 3/2007 | Johnson et al. | |
| 7,226,503 B2 | 6/2007 | Anselmann | |
| 7,235,127 B2 | 6/2007 | Kunstmann et al. | |
| 7,238,424 B2 | 7/2007 | Raksha et al. | |
| 7,241,503 B2 | 7/2007 | Noguchi | |
| 7,258,900 B2 | 8/2007 | Raksha et al. | |
| 7,303,622 B2 | 12/2007 | Loch et al. | |
| 7,318,861 B2 | 1/2008 | Bagala, Sr. et al. | |
| 2002/0160194 A1 | 10/2002 | Phillips | |
| 2003/0005859 A1 * | 1/2003 | Andes et al. | 106/403 |
| 2003/0039836 A1 * | 2/2003 | Pfaff et al. | 428/404 |
| 2003/0097965 A1 | 5/2003 | Heider | |
| 2003/0177950 A1 | 9/2003 | Schoen | |
| 2005/0142084 A1 | 6/2005 | Ganguly et al. | |
| 2005/0154082 A1 | 7/2005 | DeLuca, Jr. et al. | |
| 2005/0186423 A1 | 8/2005 | Johnson | |
| 2006/0070552 A1 | 4/2006 | Loch et al. | |
| 2006/0223910 A1 | 10/2006 | Bagala | |
| 2007/0026229 A1 | 2/2007 | Johnson | |
| 2007/0028799 A1 | 2/2007 | Kniess et al. | |
| 2007/0031683 A1 | 2/2007 | Morohashi et al. | |
| 2007/0032573 A1 | 2/2007 | Yanagase et al. | |
| 2007/0034112 A1 | 2/2007 | Mronga | |
| 2008/0124575 A1 | 5/2008 | Hollman et al. | |
| 2008/0170830 A1 | 7/2008 | Guan et al. | |

FOREIGN PATENT DOCUMENTS

| | | |
|---|---|---|
| DE | 31 51 354 | 7/1983 |
| DE | 32 35 017 | 3/1984 |
| DE | 33 34 598 | 4/1985 |
| DE | 40 30 727 | 4/1992 |
| DE | 197 46 263 | 4/1999 |
| DE | 10 2006/06099 | 6/2008 |
| EP | 0 090 259 | 10/1983 |
| EP | 0 290 908 | 11/1988 |
| EP | 0 632 109 | 1/1995 |
| EP | 0 634 459 | 1/1995 |
| EP | 0 649 886 | 4/1995 |
| EP | 0 913 431 | 5/1999 |
| EP | 1 666 541 | 6/2006 |
| JP | 58 164653 | 9/1983 |
| JP | 07-330948 | 12/1995 |
| WO | WO 96/32446 | 10/1996 |
| WO | WO 97/29059 | 8/1997 |
| WO | WO 99/57204 | 11/1999 |
| WO | WO 01/92425 | 12/2001 |
| WO | WO 2008/077487 | 7/2008 |
| WO | WO 2008/156948 | 12/2008 |

OTHER PUBLICATIONS

International Preliminary Report on Patentability and Written Opinion dated Aug. 24, 2010 for Application No. PCT/US09/033201.

Office Action dated Sep. 16, 2010 for U.S. Appl. No. 11/931,534.

Office Action dated Sep. 17, 2010 for U.S. Appl. No. 11/931,415.

Office Action dated Sep. 27, 2010 for U.S. Appl. No. 11/931,473.

Notice of Allowance dated Aug. 24, 2010 for U.S. Appl. No. 11/765,614.

Buxbaum, G . et al., Industrial Inorganic Pigments, $3^{rd}$ Ed. (2005) Weinheim: Wiley-VCG Verlag GmbH & Co KGaA, pp. 7-50 & 195-273.

International Search Report dated Sep. 10, 2009 for Application No. PCT/US08/087640.

Li, Y. et al., "Hydrothermal Synthesis of Ultrafine $\alpha$—$Fe_2O_3$ and $Fe_3O_4$ Powers," Materials Research Bulletin, vol. 33(6) (Jun. 1, 1998) pp. 841-844.

Office Action dated Nov. 14, 2008 for U.S. Appl. No. 12/016,341.

Office Action dated May 11, 2009 for U.S. Appl. No. 12/016,341.

Office Action dated Nov. 19, 2009 for U.S. Appl. No. 12/016,341.

Abstract for DE 2215 191, also published as GB1348878.
Abstract for DE 31 51 354, also published as US 4,494,993.
Abstract for DE 3235 017, also published as US 4,482,389.
Abstract for DE 33 34 598, also published as US 4,544,415.
Abstract for DE 40 30 727.
Abstract for EP 0 090 259, also published as US 4,490,179.
Abstract for EP 0 632 109.
Abstract for JP 58 164653.
Harding, P.H., J. of Adhesion Science Technology, vol. 11(4) p. 471-493.
Ponjee, J.J., Philips Technical Review, vol. 44(3) p. 81.
International Search Report dated Sep. 10, 2009 for Application No. PCT/US2008/064243.
Written Opinion dated Sep. 10, 2009 for Application No. PCT/US2008/064243.

Jan Subrt, et al., "Uniform Particles with a Large Surface Area Formed by Hydrolysis of $Fe_2(SO_4)_3$ with Urea," Materials Research Bulletin, 1999, p. 905-914, vol. 34, No. 6.
Miyoshi, "Overall Review of Surface Modification Technology," 2000, Report from PCI Asia.
Tan Junru, et al.; "The preparation and characteristics of a multi-cover-layer type, blue mica titania, pearlescent pigment," Dyes and Pigments, 2003, pp. 93-98, vol. 56.
Vaclav Stengl, et al., "The preparation and characteristics of pigments based on mica coated with metal oxides," Dyes and Pigments, Mar. 2003, pp. 239-244, vol. 58.
Junru Tan, et al.; "Preparation and conductive mechanism of mica titania conductive pigment," Dyes and Pigments, 2003, pp. 107-114, vol. 62.

* cited by examiner

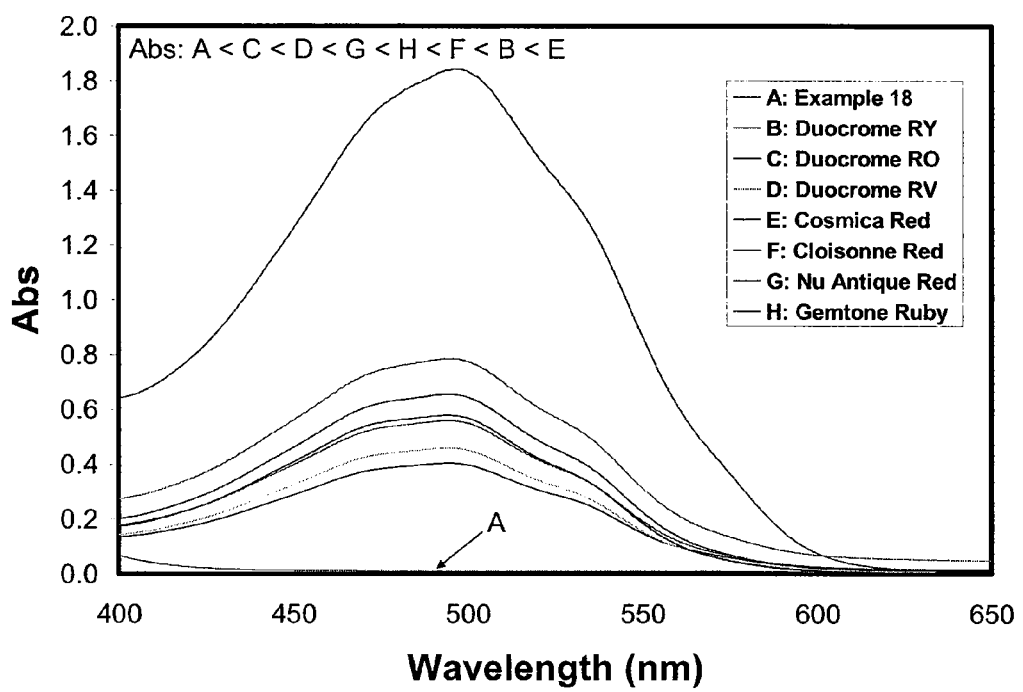
Figure 2. Absorbance measurements of the filtrate solution for each red pearlescent pigment analyzed for acid resistance.

COSMETIC COMPRISING MULTI-COLORED LUSTROUS PEARLESCENT PIGMENTS

CROSS REFERENCE TO RELATED APPLICATIONS

The present application is a divisional of U.S. Ser. No. 11/931,658, filed on Oct. 31, 2007, now U.S. Pat. No. 8,221,536, which is a continuation-in-part of U.S. Ser. No. 11/765,614, filed on Jun. 20, 2007, now U.S. Pat. No. 7,850,775, which claims the benefit of the provisional patent application Ser. No. 60/865,042, filed on Nov. 9, 2006, the disclosures of which are hereby incorporated by reference in their entirety.

BACKGROUND OF THE INVENTION

The present invention relates, in general, to multi-colored lustrous pearlescent pigments.

Along with gem stones (e.g., diamond, ruby, emerald, topaz, opal, jade), and precious metals (e.g., gold, silver, platinum), pearls are among the most prized possessions (or luxury items) for human beings for millenniums. Beside their natural beauty, the brilliant color and luster, they are often associated with social status and level of well-being. As a result, and not surprisingly, the trend of cosmetics makeup is to emulate or recreate these "natural" and "aesthetic" appearances of pearl, gem and precious metals with less expensive materials such as interference pigments (e.g., metal oxide coated mica). The most common types of pearlescent pigments are micronized titanium dioxide, metal oxide coated mica, metal oxide coated alumina, metal oxide coated silica, basic lead carbonate, bismuth oxychloride, and natural fish silver.

Metal oxide coated mica pigments are characterized by excellent optical, chemical, mechanical, toxicological, and environmental properties. Natural or synthetic mica, and alternative supports, such as aluminum flakes, or $SiO_2$ platelets, can be used alone, or as a support for titanium dioxide, iron oxide ($Fe_2O_3$ or $Fe_3O_4$), iron ferrocyanide (Iron Blue or Prussian Blue), tin oxide, and chromium oxide. The color space defined by these coated mica-based pigments is based on the type of coating (e.g. metal oxide, colorant, etc.) used, the layer thickness, and the number of coated layers.

Among the natural pearls, the most expensive are black pearls, which come with various undertone and color flops. To faithfully emulate this aesthetic optical effect in cosmetic makeup is one of the top challenges facing a cosmetic pigment maker and formulator. The traditional approach to these pigments is to blend dark solid-color inorganic pigment (e.g., carbon black) with white platy pearlescent pigments (e.g., $TiO_2$ coated mica, $TiO_2$ coated borosilicate, $TiO_2$ coated alumina). The platy interference pigment provides the luster, brilliance (reflection), transparency and depth of field. The solid-color pigment(s) provide(s) the dark undertone and surface coverage. However, this type of blend usually appears to be much "dirtier", "lack luster", and "lack transparency" compared to the natural pearl. The primary reason for that is fouling of the smooth surface of white pearlescent pigment by the solid-color pigment granules, which leads to light scattering and disruption of light interference.

Metal oxide coated platelet pigments may be magnetic or exhibit magnetic susceptibility. When placed into a liquid coating, regions of the coated pigment may be aligned by an externally applied magnetic field and produce a goniochromatic, or angle dependent optical effect. This effect may be used to create an impression of a two- or three-dimensional image. After the pigments have been aligned, the coating may be cured to solidify the optical effect. Examples of pigments and methods of aligning them are discussed in U.S. Pat. No. 6,589,331, U.S. Pat. No. 6,902,807, U.S. Pat. No. 5,223,360, U.S. Pat. No. 6,759,097, and U.S. Pat. No. 7,258,900. However, the magnetic pigments are significantly limited in terms of color space. The typical colors available are metallic black, grey shades, or bichromic shades characterized by a black or reddish brown absorbance color combined with a weak interference color.

A need exists to expand the existing color space of metal oxide coated pigments to more vibrant, lustrous colored shades, as well as, antique dark pearlescent shades, using a processing method that allows for optimal control of color and opacity. In addition, a need exists for more colorful magnetic pigments that have a larger color contrast between aligned and non-aligned pigments.

BRIEF SUMMARY OF THE INVENTION

The invention overcomes the above-noted and other deficiencies of the prior art by providing a pearlescent pigment comprising a substrate and a first layer, wherein the first layer comprises iron oxide, wherein the iron in the iron oxide comprises from about 10% to about 20% Fe(II), and from about 80% to about 90% Fe(III).

Another aspect of the invention is a pearlescent pigment, wherein the pigment is an inorganic material and the color of a homogeneous coating of the pigment, measured over a white background, is selected from the group consisting of: a CIELAB hue angle, $h_{ab}$, from about 50 to about 80 degrees, wherein L* is not more than about 85, and the chroma value is greater than 22; a CIELAB hue angle, $h_{ab}$, from about 80 to about 275 degrees, wherein L* is not more than about 80, and the chroma value is greater than about 10; and a CIELAB hue angle, $h_{ab}$, from not less than about 275 to not more than about 50 degrees, wherein L* is not more than about 85, and the chroma value is greater than about 9.

Another aspect of the invention is a pearlescent pigment, wherein the pearlescent pigment is an inorganic material and the color of a homogeneous coating of the pigment, measured over a white background, has a CIELAB L* value of about 30 or less and a chroma value of about 3 or less.

Another aspect of the invention is a pearlescent pigment, wherein the pigment is prepared by coating a substrate with a metal oxide to form a first layer, and reducing the metal oxide of the first layer, wherein only about 10% to about 20% of the metal is reduced.

Another aspect of the invention is a pearlescent pigment, wherein the homogeneous pearlescent pigment is an inorganic material and the ΔE* between the magnetically aligned and non aligned pigment as measured over a white background is not less than 20.

Another aspect of the invention is a process for reducing a metal oxide coated substrate with a hydrogen source in the presence of a noble metal catalyst.

Another aspect of the invention is a process for making a pearlescent pigment, comprising reducing an iron oxide coated substrate with a hydrogen source, wherein only about 1% to about 30% of the iron is reduced.

Another aspect of the invention is a highly active catalyst, comprising a nanoparticulate noble metal in a polyvinylpyrrolidone (PVP) polymer, or other polymer.

Another aspect of the invention is a cosmetic formulation containing a pearlescent pigment comprising a substrate and a first layer, wherein the first layer comprises iron oxide, wherein the iron in the iron oxide comprises from about 10% to about 20% Fe(II), and from about 80% to about 90% Fe(III).

Another aspect of the invention is a cosmetic composition containing a pearlescent pigment comprising a substrate and a first layer, wherein the first layer contains iron oxide, wherein the iron of the iron oxide has from about 1% to about 30% Fe(II) and from about 70% to about 99% Fe(III).

Another aspect of the invention is a paint or ink composition containing a pearlescent pigment comprising a substrate and a first layer, wherein the first layer comprises iron oxide, wherein the iron of the iron oxide has from about 1% to about 30% Fe(II) and from about 70% to about 99% Fe(III).

Another aspect of the invention is a plastic composition containing a pearlescent pigment comprising a substrate and a first layer, wherein the first layer comprises iron oxide, wherein the iron of the iron oxide has from about 1% to about 30% Fe(II) and from about 70% to about 99% Fe(III).

These and other objects and advantages of the present invention shall be made apparent from the accompanying drawings and the description thereof.

BRIEF DESCRIPTION OF THE FIGURES

FIG. 2 is the visible spectra of the filtrates of the pigments tested in Example 18

DETAILED DESCRIPTION OF THE INVENTION

Figure 1:
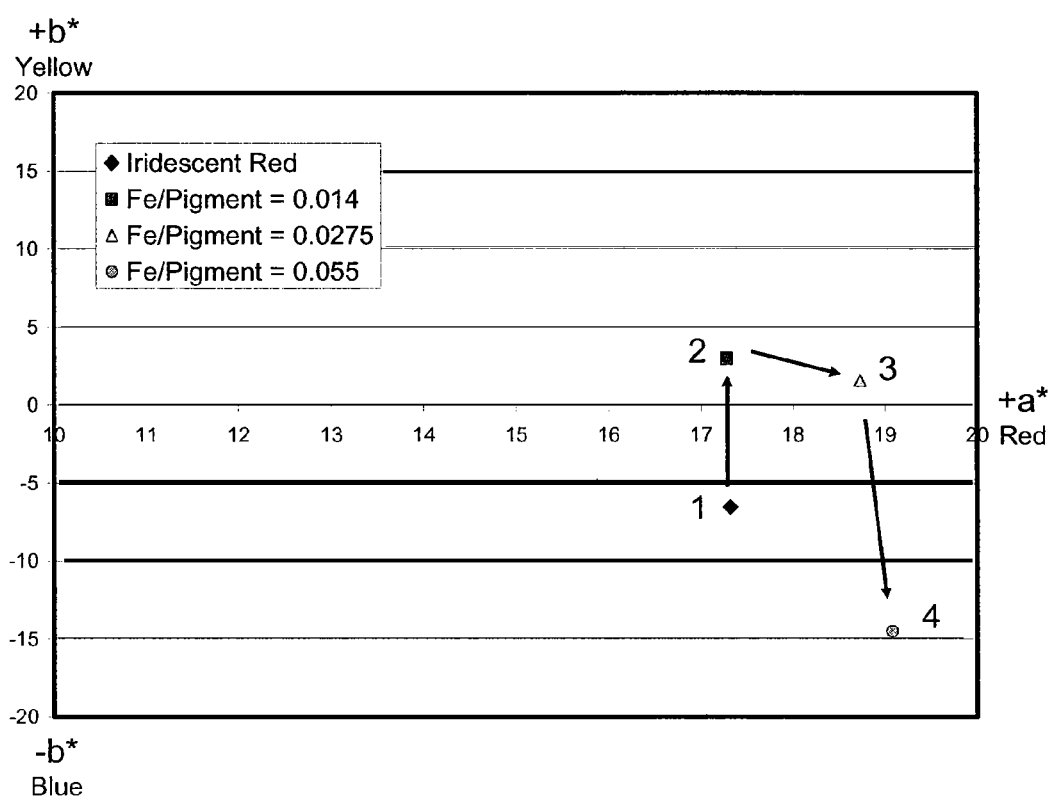
FIG. 1 is a graph of the CIELAB a* and b* color coordinates of Examples 14-16 as measured against a black background.

The present invention relates to lustrous, pearlescent pigments with controlled opacity, comprising a substrate and a first layer, wherein the first layer comprises iron oxide, wherein the iron in the iron oxide comprises from about 1% to about 30% Fe(II) and from about 70% to about 99% Fe(III).

Iron oxide coated substrates exhibit intensely colored pearlescent pigments with high luster. Varying the substrate, the iron oxide layer thickness, and the amount of Fe(II) and Fe(III) in the layer will change the color, luminosity, and transparency of the pigment. The mean thickness of the first layer may be from about 1 nm to about 350 nm, from about 10 nm to about 350 nm, or from about 10 nm to about 250 nm.

In one embodiment, the pigment may comprise a second layer located between the substrate and the first layer, wherein the second layer has a refractive index of greater than about 1.6 or less than about 1.4. The second layer may have a refractive index equal to or greater than about 1.8. Examples of compounds that may be used as the second layer are: $TiO_2$, $Fe_2O_3$, $ZrO_2$, $SnO_2$, $Cr_2O_3$, BiOCl, and ZnO. The second layer may comprise one or more materials. The second layer may be $TiO_2$. The second layer may be an iron oxide, such as $Fe_2O_3$, $Fe_3O_4$, FeOOH, FeO, and $Fe(OH)_3$. The mean thickness of the second layer may be from about 50 nm to about 800 nm, or from about 100 nm to about 600 nm.

In another embodiment, titanium oxide coated mica pigments exhibit pearlescent effects resulting from reflection and light interference. The interference color and luster is dependent on the thickness of the $TiO_2$ surface layer and its corresponding surface roughness. This initial interference color of the pigment, prior to the coating of the first layer is apparent when viewed against a black background. It has been surprisingly discovered that FeOOH deposition followed by reduction results in the advancement of the interference color and a significant increase in opacity of $TiO_2$ coated platelet-like pigments. This process transforms the transparent, $TiO_2$ coated mica, into a lustrous colored pearlescent pigment with increased opacity. The thickness of the deposited FeOOH layer controls the magnitude of the color progression and opacity. For relatively thick FeOOH layers, the interference color progresses to the next shade and the pigment approaches complete opacity.

In order to improve the light, water repellency, weather stability, texture, and dispersion ability, it is frequently advisable to subject the finished pigment to surface treatment, depending on the area of application. Examples of surface treatments are methicone (poly(oxy(methylsilylene))), metal soap, fatty acid, hydrogenated lecithin, dimethicone (polydimethylsiloxane), fluorinated compounds, amino acids, N-acylamino acids, glyceryl rosinates, silanes, and combinations. Many of the processes are described in U.S. Pat. No. 6,790,452; U.S. Pat. No. 5,368,639; U.S. Pat. No. 5,326,392; U.S. Pat. No. 5,486,631; U.S. Pat. No. 4,606,914; U.S. Pat. No. 4,622,074; German Patent 22 15 191; DE-A 31 51 354; DE-A 32 35 017; DE-A 33 34 598; DE 40 30 727 A1; EP 0 649 886 A2; WO 97/29059; WO 99/57204; U.S. Pat. No. 5,759,255; EP 0090259; EP 0 634 459; WO 99/57204; WO 96/32446; WO 99/57204; U.S. Pat. No. 5,759,255; U.S. Pat. No. 5,571,851; WO 01/92425; U.S. Pat. No. 5,472,491; J. J. Ponjee, Philips Technical Review, Vol. 44, No. 3, 81 ff; and P. H. Harding J. C. Berg, J. Adhesion Sci. Technol. Vol. 11 No. 4, pp. 471-493. This post-coating may further increase the chemical stability or simplify handling of the pigment, in particular incorporation into various media. In order to improve the wettability, dispersibility and/or compatibility with the user media, functional coatings of $Al_2O_3$ or $ZrO_2$ or mixtures thereof may be applied to the pigment surface.

In one embodiment, coupling agents may be used to form an outer layer on the pearlescent pigment. Suitable coupling agents are disclosed in EP 632 109. Examples include, silanes, zirconium aluminates, zirconates, and titanates. The silanes may possess the structure Y—$(CH_2)_n$—$SiX_3$ in which n is 2-8, Y is an organofunctional group, e.g. an amino, methacrylic, vinyl, alkyl, aryl, halogen and/or epoxy group, and X is a silicon-functional group which following its hydrolysis reacts with active sites of an inorganic substrate or by condensation with other silicon compounds. This group Y may comprise, for example a hydroxy, a halogen or an alkoxy group.

In addition to these substantially hydrophilic coupling agents, it is also possible to use hydrophilic silanes, especially the aryl-, alkyl- and fluoroalkyl-substituted di- and trimethoxysilanes. These include, for example, phenethyltrimethoxysilane, propyltrimethoxysilane, butyltrimethoxysilane, isobutyltrimethoxysilane, hexyltrimethoxysilane, octyltrimethoxysilane, 1H,1H,2H,2H-perfluorodecyltrimethoxysilane and (3,3,3-trifluoropropyl)methyldimethoxysilane. The concentration of coupling agents may be 0.2-1.2% by weight with respect to the base pigment.

In one embodiment, the substrate is platelet-like and may have a mean thickness of about 0.05 to about 1.5 µm and a mean width of about 1 to about 750 µm. The substrate may have a mean width of about 10 to about 60 µm, about 5 to about 25 µm, about 10 to about 100 µm, about 40 to about 250 µm, or about 95 to about 730 µm.

As an example, when a relatively thin FeOOH coating on an iridescent blue $TiO_2$ coated laminar substrate (such as SunPearl Iridescent Blue by SunChemical) is reduced by hydrogenation, a semi-opaque lustrous blue-green or turquoise pearlescent pigment results (see Example 26). However, using this same iridescent blue substrate a thicker FeOOH coating will result in a lustrous green or olive pearlescent shade with increased opacity when reduced using similar hydrogenation conditions (see Example 27). This color advancement trend is applicable to many shades of $TiO_2$ coated laminar substrates. Therefore, more opaque blue pearlescent shades may be produced by reduction of iridescent violet $TiO_2$ coated substrates (such as SunPearl Iridescent Violet by SunChemical) containing thick FeOOH coatings (see Example 23). Likewise, less opaque green shades may be produced by reduction of iridescent green $TiO_2$ coated substrates (such as SunPearl Iridescent Green by SunChemical) having relatively thin FeOOH surface layers (see Example 8).

The synthesis of a particular colored pearlescent pigment begins with selection of the proper substrate material. The substrate may be comprised of natural mica, synthetic mica, glass flakes, $Al_2O_3$ platelets, $SiO_2$ platelets, BiOCl, borosilicate, synthetic alumina, and boron nitride. Such substrates may be multilayer materials, i.e. include materials of different refractive indices. The substrate may comprise mica. The pearlescent pigment may comprise a mixture of different substrates. Furthermore, the substrate may be made of identical or different flakes which differ in particle size.

The first step in forming a colored pearlescent pigment is to coat the substrate, or metal oxide coated substrate with a layer of non-annealed FeOOH, which is usually pale yellow in color. For the reasons of decreased crystallinity and higher surface area (porous microstructure), non-annealed FeOOH may be reduced to an iron oxide (FeO, FeO—$Fe_2O_3$, $Fe_3O_4$) under more mild reaction conditions, as compared to the more crystalline $Fe_2O_3$. The methods of deposition (or precipitation) of FeOOH or $Fe(OH)_3$ onto substrates are well known in the literature, for example as shown in *Dyes and Pigments*, 58 (2003), 239-244, U.S. Pat. No. 3,926,659, and in many scientific papers and patents particularly by Merck, Engelhard, and BASF. It is possible to start from a pre-coated substrate and coat this substrate with a metal oxide. Alternatively, the process may start from the substrate itself and a single coating may be used to reach the correct amount of iron oxide. Metal oxides other than FeOOH may used to the coat the substrate, or metal oxide coated substrate.

The basic principle of deposition is as follows: $Fe^{3+}$ precursors such as ferric chloride, ferric sulfate, or both, are dissolved in an acidic medium containing the substrate. As the pH is increased by the addition of bases such KOH, NaOH, LiOH, and ammonia; $Fe^{3+}$ ions are precipitated out as either colloidal FeOOH particles, or dense aggregates depending on the pH control profile, temperature and concentration, and in some case the presence of electrical field. In the presence of substrates with affinity to FeOOH, the colloidal particles can quickly form a uniform film on the substrate. The bonding between the deposited layer and substrate is usually a combination of metal oxide covalent bonds and hydrogen bonds. For example, in the case of making an antique burgundy pearlescent pigment, the substrate is hematite (red calcined $Fe_2O_3$) coated mica, which has extremely good affinity to FeOOH.

The traditional precipitation process utilizing KOH and NaOH is called a heterogeneous hydrolysis process. However, more recently, a newer process called homogenous hydrolysis, utilizes urea as an in situ generated base. This process is said to produce a smoother and more transparent metal oxide film as shown in *Dyes and Pigments* 58 (2003) 239-244, and *Materials Research Bulletin* (1999), vol. 34, no. 6, 905-914. The use of ferric sulfate may produce coarser particles, and weaker luster than ferric chloride. A computer-programmed rate-control heater may be used to better control the decomposition rate of urea, which in turn controls the rate of ammonia (base) generation. When the base generation rate is zero order (i.e., constant), the FeOOH colloids will nucleate and grow at a constant rate, and precipitate onto the substrate at a constant rate as well. As a result, a highly uniform film can be generated. At 80° C.-90° C., the urea hydrolysis is nearly zero order. This temperature range may be useful as the plateau (holding) temperature of the process. The amount of urea used is just enough to bring the final hydrolyzed solution pH to be between 6 and 8, in order to minimize the amount of free $Fe^{3+}$ precursor left in the solution. $Fe^{3+}$ is known to be at its lowest solubility around pH 8.

Depositing FeOOH by the Fe(III)-urea homogeneous hydrolysis may lead to uniform layers of FeOOH on the surface of the titanium dioxide coated mica substrates, which results in neon shaded pearlescent pigments (neon green-gold, neon pink, neon silver gold, etc.) that are not currently available commercially.

After deposition of a thin layer of FeOOH onto the colored substrate, the pigments are recovered from the solution by filtration. The pigments are washed multiple times with deionized water to remove residual urea, followed by drying to remove residual moisture. Following sufficient drying, the dry pigments are ready for reduction. Hydrogenation may be used to reduce the FeOOH layer. The resultant iron oxide (FeO, FeO—$Fe_2O_3$, $Fe_3O_4$) layer is typically darker in color, depending on the degree of reduction, thickness of the layer, and any other layers. Generally speaking, the more aggressive the hydrogenation conditions or the thicker the layer, the darker the final pigment will be. However, an overly thick iron oxide (FeO, FeO—$Fe_2O_3$, $Fe_3O_4$) layer will lead to some loss of transparency and luster. The reduction is performed so that the iron of the iron oxide typically comprises from about 1% to about 30% Fe(II) and from about 70% to about 99% Fe(III). The reduction may be performed so that the iron of the iron oxide comprises from about 12% to about 18% Fe(II) and from about 82% to about 88% Fe(III). The reduction may be performed so that the iron of the iron oxide comprises from about 14% to about 16% Fe(II) and from about 84% to about 86% Fe(III). In one embodiment, the amount of iron, in the iron oxide, is about 1% to about 15% of the weight of the pearlescent pigment.

Other metal oxides maybe reduced by this procedure. The reduction may be performed so that about 1% to about 30% of the metal in the metal oxide has been reduced. The reduction may be performed so that about 12% to about 18% of the metal in the metal oxide has been reduced. The reduction may be performed so that about 14% to about 16% of the metal in the metal oxide has been reduced. In one embodiment, the amount of metal, in the metal oxide, is about 1% to about 15% of the weight of the pearlescent pigment.

Homogeneous hydrogenation of suspensions containing metal oxide coated mica-based pigments allows much greater control of the oxidation state of the deposited iron oxide layers, compared to conventional high temperature calcination in a reducing ($H_2/N_2$) atmosphere. Thus, this processing technique may allow more precise control over pigment color and luster. In addition, the two step process of metal oxide deposition followed by liquid phase hydrogenation may yield pearlescent pigments with a smooth texture and improved rub-resistance relative to existing methodologies (e.g. mixtures, etc.). An example of the metal oxide that may be reduced is FeOOH.

One method of reduction uses a liquid-phase hydrogenation set-up consisting of three main components: 1) the hydrogen reservoir (equipped with $N_2$ purging); 2) a pressurized reaction chamber (with a 45° pitch agitation blade and an electrical heating mantle); and 3) a blow-out collector reservoir in case of over-pressure situation. The system is fully enclosed to minimize the risk of gas explosion. The pigments are first dispersed in a non-oxidizing (or mildly reductive) liquid, which has a reasonable $H_2$ gas solubility. Generally speaking, the higher the gas pressure, the higher the $H_2$ concentration in the carrying medium, and therefore the faster the reduction reaction. Higher temperatures and the addition of a noble metal catalyst also speed up the reaction. The degree of reduction, or the lightness (or darkness) of the final pigment are most effectively controlled by the length of reduction time and catalyst loading.

Some examples of solvents are PEG 400 (polyethylene glycol of molecular weight 425 g/mol) and NMP (N-methylpyrrolidone). Other solvents or liquids such as ethylene glycol, PEG 200, dimethylformamide and water can also be used. PEG 400 is most favored due to its high chemical stability (i.e., reusable for many runs), high boiling point (i.e., enabling high temperature reduction), low vapor pressure, low flammability, high $H_2$ solubility, good wetting power to the pigment (i.e., excellent dispersion and maximum surface exposure to $H_2$), good wetting power to the catalyst (i.e., maximize catalytic surface), and moderate viscosity (45 cP) for the ease of processing, which should be high enough to keep mica pigments from settling even under gentle agitation, and low enough to be filtered out under mild vacuum filtration condition. NMP may also be used. The hydrogenation pressure may be from atmospheric pressure, or above atmospheric pressure to about 70 bar. The pressure may be from about 10 bar to about 40 bar, or from about 10 to about 25 bar. The temperature may be from room temperature to about 220° C., or from 200-220° C., below the degradation temperature of the solvents. The agitation is usually kept below about 300 RPM to avoid fragmenting the pigment. The mica based pigments are usually very fragile and can break under high shear. Fragmentation usually leads to the rise of opacity and loss of luster. The concentration of the catalyst may be about 0.001 to about 0.2 g of catalyst per kilogram of liquid medium. In one embodiment the concentration of the catalyst may be about 0.01 to about 0.08 g of catalyst per kilogram of liquid medium.

Examples of noble metal catalysts include, but are not limited to Pd, Pt, $PtO_2$ (Adam's catalyst), Rh, Au, Ag, and Ta. The catalyst may be oxides, hydroxides or other derivatives of noble metals. The catalyst can come in supported or unsupported forms. Examples of supported forms include, but are not limited to Pd and Pt metals deposited onto charcoal or carbon based supports (coconut shell, etc.), alumina, zeolite or other inorganic substrates (support). The size of support can range from several millimeters to as small as 10-20 microns. Due to the higher surface to volume ratio, catalysts on smaller support can have a higher metal loading and thus higher catalytic activity. However, due to the size and density similarity to interference pigments, (i.e., 25-75 micron, SG of 3-5), catalysts of small support can be difficult to separate from the pigment, recover and reuse. The use of supported catalysts the size of about 1 mm and above, can be easily separated from pearlescent pigments by dry sieving using sieves of 80-120 mesh size. The large-support catalysts, including but not limited to Escat® 3 mm (Pt on alumina) are easily separated; they have relative low efficiency, and thus are useful for shallower hydrogenation that produces lighter color antique pearls such as antique copper and antique bronze.

Nanoparticulate metal catalysts are useful for deep hydrogenation to obtain extremely dark color. In one embodiment, commercially obtained bulk $PtO_2$ powder (usually 10-50 micron diameter) is wet milled with PEG400 in an intensive media mill using 0.5 mm zirconia media for 8 to 16 hours. The final particle size is submicron (ie., colloidal size), and the $PtO_2$ can suspend in PEG 400 liquid for a couple days without settling. Since the majority of the interference pigment will settle in PEG 400 within an hour or so, sedimentation may be used as a separation process to recover colloidal $PtO_2$ from the pigment slurry. The majority of colloidal $PtO_2$ will remain in supernatant phase to be decanted and reused. Such method provides for an efficient liquid-phase hydrogenation of metal oxide coated mica pigments.

In one embodiment the catalyst nanoparticulate has a mean diameter from about 53 to about 55 nm. The median particle size may be about 40 nm.

A colloidal fluid of stabilized metal nanoparticles, such as Pt nanoparticles (Pt—NP) may be used as the catalyst for hydrogenation. Pt—NP catalytic fluid is prepared by a polymer stabilized direct-reduction method. The Pt nanoparticles are of 2-5 nm in size, and are stabilized by polyvinylpyrrolidone (PVP) polymer. This embodiment offers several benefits over micronized $PtO_2$ catalyst and industrially available hydrogenation catalysts mentioned above. First, it is thought that the extremely large surface area of Pt colloid allows for the use of less catalyst, and much more intimate contact between the catalyst and the substrate. Secondly, a small particle size and the presence of a lubricating polymer (PVP), help reduce the friction between the substrate and catalyst, which may lead to better preservation of surface smoothness and luster of the pigment. Third, this catalytic fluid is thermodynamically stable. The long shelf-life is a big advantage over the micronized $PtO_2$ catalyst, which requires periodically re-milling to sustain catalytic efficiency.

After hydrogenation, the pigment is subjected to an optional washing step to remove the Pt residue. PVP, a known chelating agent to Pt and a reducing agent to platinum salt, is useful as a 10% PVP aqueous washing solution to remove the free Pt—NP in the supernatant, Pt—NP absorbed onto substrate and any trace of Pt ions that might be present.

The deposition of FeOOH followed by hydrogenation may be utilized to progress the interference color associated with pearlescent, $TiO_2$ coated, mica-based pigments. Transparent, pearlescent $TiO_2$ coated pigments may be transformed into lustrous colored pearlescent pigments using the described methodology. For relatively thin FeOOH deposition, hydrogenation results in pigments characterized by the same interference color with increased opacity. The interference color may be progressed to the next shade (for instance, from violet to blue or blue to green) through reduction of relatively thick FeOOH coatings. This process also significantly increases the opacity of the resulting pearlescent pigment. Thus, various vibrant, multi-colored pigments may be produced in all four quadrants of the CIELAB color space with controlled opacity allowing for significantly improved formulation flexibility.

In one embodiment of a black/antique pearlescent pigment, the synthesis starts with choosing an appropriate substrate. The choice of substrate affects the undertone and transparency of color of the black/antique pearl interference pigment. For example, to yield an antique burgundy look, it is important to choose a substrate with deep red or deep maroon color, such as hematite (i.e., high temperature calcined $Fe_2O_3$) coated mica. This undertone in combination with an iron oxide (FeO, FeO—$Fe_2O_3$, $Fe_3O_4$) top layer will produce various shades of burgundy colors. $Fe_2O_3$ or $TiO_2$ coated synthetic or natural mica has colors ranging from red to yellow and blue to green. The color of substrate dictates the undertone of final pearl appearance. It is also desirable to choose a substrate with high transparency so that it can faithfully emulate the "airy" look of high quality natural pearl. Generally speaking synthetic mica (such those made by CQV), glass flakes layer (for instance from Nippon Sheet glass), borosilicate and synthetic alumina substrates are preferred over natural mica for higher transparency. Such substrates may be multilayer materials i.e. include materials of different refractive indices.

In one embodiment the pearlescent pigment is an inorganic material, and the color of a homogeneous coating of the pigment, measured over a white background, is selected from the group consisting of: a CIELAB hue angle, $h_{ab}$, from about 50 to about 80 degrees, wherein L* is not more than about 85, and the chroma value is greater than 22; a CIELAB hue angle, $h_{ab}$, from about 80 to about 275 degrees, wherein L* is not more than about 80, and the chroma value is greater than about 10; and a CIELAB hue angle, $h_{ab}$, from not less than about 275 to not more than about 50 degrees, wherein L* is not more than about 85, and the chroma value is greater than about 9.

In one embodiment the pearlescent pigment is an inorganic material, and the color of a homogeneous coating of the pigment, measured over a white background has a CIELAB hue angle, $h_{ab}$, from about 50 to about 80 degrees, wherein L* is not more than about 85, and the chroma value is greater than 22. The L* may be not more than about 80, about 75, or about 70. The chroma value may be greater than about 24, about 26, or about 28. In one embodiment the CIELAB hue angle, $h_{ab}$, is from about 50 to about 65 degrees.

In one embodiment the pearlescent pigment is an inorganic material, and the color of a homogeneous coating of the pigment, measured over a white background has a CIELAB hue angle, $h_{ab}$, from about 80 to about 275 degrees, wherein L* is not more than about 80, and the chroma value is greater than about 10. The L* may be not more than about 75, about 70, or about 65. The chroma value may be greater than about 12, about 14, or about 16.

In one embodiment the pearlescent pigment is an inorganic material, and the color of a homogeneous coating of the pigment, measured over a white background has a CIELAB hue angle, $h_{ab}$, from not less than about 275 to not more than about 50 degrees, wherein L* is not more than about 85, and the chroma value is greater than about 9. The L* may be not more than about 80, about 75, or about 70. The chroma value may be greater than about 11, about 13, or about 15.

In one embodiment the pearlescent pigment is blue, with a CIELAB hue angle, $h_{ab}$, from about 170 to about 275 degrees, measured over a white background using a D65 illuminant and a 10 degree observer. Blue pearlescent pigments may be produced that do not contain iron blue (ferric ferrocyanide), allowing the pigment to be used in cosmetic applications involving the lip area, such as lip gloss, lipstick, and other lip formulations. In addition, the blue pearlescent pigments are more stable than ferric ferrocyanide, which decomposes in alkaline pH resulting in pigment bleeding and marked changes in pigment color. Another advantage of the blue pearlescent pigments is that they do not restrict the pigment to the color space defined by ferric ferrocyanide. Iron Blue is a powerful colorant that only allows the pigment designer to formulate pigments within a well defined, narrow color space and restricts formulation flexibility, see *Dyes and Pigments* 56 (2003) 93-98.

In one embodiment the pearlescent pigment is green, with a CIELAB hue angle, $h_{ab}$, from about 80 to about 170 degrees, measured over a white background using a D65 illuminant and a 10 degree observer. Green pearlescent pigments may be produced that do not contain chromium oxide, allowing the pigment to be used in cosmetic applications involving the lip area, such as lip gloss, lipstick, and other lip formulations. Most commercially available green pearlescent pigments are based on chromium oxide deposition, U.S. Pat. No. 6,485,556.

In one embodiment the pearlescent pigment is red, pink, or violet, with a CIELAB hue angle, $h_{ab}$, from not less than about 275 to not more than about 50 degrees, measured over a white background using a D65 illuminant and a 10 degree observer. Red, pink, or violet mica-based pearlescent pigments may be produced that do not contain carmine. Carmine is a colorant used extensively in the cosmetic industry either directly or combined with pearlescent pigments (such as in Cloisonné® Red by Engelhard/BASF). It is extremely sensitive to UV exposure and may fade over time. Carmine is also unstable in acidic environments. It is often characterized by colorant bleeding in cosmetic formulations, such as nail polish. In addition, carmine (which is extracted from insects) has been linked to numerous reports of allergic reactions, including anaphylaxis. The development of carmine-free red, pink and violet shades is particularly advantageous because it offers formulators a more stable and hygienic alternative. In one embodiment the pearlescent pigment does not contain carmine.

In another embodiment, the pearlescent pigment has a HPI of less than about 1 when measured in a 76 μm thick film formed from 10 wt % of the pigment in acrylic enamel. The HPI may be less than about 0.5. The HPI may range from about 0.05 to about 0.5.

There are relatively few dark colored (or antique-looking) pearlescent pigments currently offered in the market, examples of such are: Timica® and Cloisonné Nu-Antique® lines by Engelhard/BASF. The existing dark pearlescent products in the market are too opaque and too dull (i.e., not enough luster), and not dark enough to emulate the natural black pearl effect (e.g., Tahiti black pearl). In addition, they exhibit an undesirable darkening effect when applied and rubbed on the skin. One method to solve these problems is to use a dark colored layer on top or beneath the interference layer as a smooth film, to minimize light scattering, and thus preserve the luster and transparency of the pigment.

In one embodiment the pearlescent pigment is an inorganic material and the color of a homogeneous coating of the pigment, measured over a white background, has a CIELAB L* value of about 30 or less and a chroma value of about 3 or less. The L* may be not more than about 28, about 25, or about 22. The chroma value may be less than about 2.5, about 2, or about 1.5. These methods have been used to produce very dark antique/black pearl interference pigments. The darkest color achieved based on a 5% pigment drawdown in a nitrocellulose varnish is in the range of about 29 to about 32 in terms of lightness value (L* value in CIE1976 color space, measured using a 10 degree observer, illuminant D65 with Specular Component Included), which is very close to the reference LENETA card black (L*=28) along with a very low chroma (typically less than 3). Titan® ST is the range of L*=64 to 65, Engelhard's Cloisonné NU-Antique Series is in the range of L*=37 to 60. In all cases, these are much lighter and less lustrous than the pigment formed by this process.

The methods described may produce pigments with better hiding power while maintaining a high luster. The pigments may have better stability than current pigments at high and low pH, and are less likely to bleed.

In one embodiment the pearlescent pigment is an inorganic material and the ΔE* of the alkaline stability for a homogeneous coating of the pigment, measured over a white background, is less than about 2.

In one embodiment the pearlescent pigment is an inorganic material and the ΔE* of the acid stability for a homogeneous coating of the pigment, measured over a white background, is less than about 4.

In one embodiment the pearlescent pigment is an inorganic material and the ΔE* of magnetically aligned and non-aligned homogeneous coatings of the pigment, measured over a white background, is not less than 20.

In one embodiment the pearlescent pigment has a magnetic susceptibility of about $0.1 \times 10^{-5}$ to $7.5 \times 10^{-5}$ m$^3$/kg.

The pigments may be magnetic or exhibit magnetic susceptibility. In fluid-based systems, such as liquid coatings or uncured plastic preparations containing these pigments, an applied magnetic field may be used to align pigments in specific regions of the coating to create images that appear to be three-dimensional. After the pigments have been aligned, the coating may be cured to solidify the image.

The three-dimensional effect is produced by the pigment particles aligned at non-parallel or intermediate angles with respect to the coating surface. In an applied electric field, the high aspect ratio platelets will align themselves such that the longest dimension of the platelet (namely, the platelet width) aligns itself along the magnetic field lines. The ability to reorient the colored particles allows them to be manipulated to specific angles resulting in a controlled three-dimensional appearance. In regions of where the field lines are perpendicular to the observer, the platelet particles will be perpendicular to the observer resulting in a jet black appearance. This extremely dark appearance is due to light scattering at the particle edges and the absence of a reflective surface. In regions devoid of an applied magnetic force, the particles align more substantially parallel to the applied coating surface resulting in the intensely colored appearance. Applying a magnetic field parallel to the coating surface will orient more of the pigments parallel to the surface resulting in a even more intensely colored appearance.

In one embodiment a cosmetic composition contains the pearlescent pigment. The cosmetic composition may be useful for make-up products for the skin, the eyes, or hair. Examples of compositions intended as make-up for the skin include eye shadows, eye liners, mascaras, body or face powder, foundations, blushes, colored creams, nail polish, lipsticks, lip gloss, hair or body gel, hair or body wash, cover sticks, lotion, concealer and foundation. Examples of cosmetic applications involving the lip area, are lip gloss, lipstick, and other lip compositions. Nail polish may be referred to as nail varnish, or nail enamel.

Pearlescent pigments may be used to produce a makeup cosmetic as described in U.S. Pat. No. 6,663,852, U.S. Pat. No. 6,451,294, and U.S. Pat. No. 6,280,714.

In one embodiment, the pigments of the composition are aligned during or after application of the composition. An example of aligning the pigments of the composition is by applied the composition with a magnetic applicator. The magnetic applicator may be used to align the magnetic particles in the cosmetic allowing control of their appearance.

General cosmetic compositions may contain preservatives, stabilizers, neutralizing agents, aqueous-phase thickeners (polysaccharide biopolymers, synthetic polymers) or fatty-phase thickeners, such as clay minerals, fillers, perfumes, hydrophilic or lipophilic active substances, surfactants, antioxidants, film-forming polymers and mixtures thereof. The amounts of these various ingredients are those conventionally employed in the fields in question and, for example, may be from 0.01 to 30% of the total weight of the composition. In one embodiment, the cosmetic composition may further comprise a binder wherein the pigment represents about 0.5% to about 99.5% of the composition.

Lip cosmetic composition may comprise any ingredient usually used in the field concerned, such as water, preferably in an amount ranging from 0 to 95% of the total weight of the composition, water-soluble or liposoluble dyes, antioxidants, essential oils, preserving agents, fragrances, neutralizing agents, liposoluble polymers, in particular hydrocarbon-based polymers such as polyalkylenes or polyvinyl laurate, gelling agents for an aqueous phase, gelling agents for a liquid fatty phase, waxes, gums, surfactants, additional cosmetic or dermatological active agents such as, for example, emollients, moisturizers (for example glycerol), vitamins, liquid lanolin, essential fatty acids, lipophilic or hydrophilic sunscreens, and mixtures thereof. The composition may also contain lipid vesicles of ionic and/or nonionic type. These ingredients (other than the water) may be present in the composition in a proportion of from 0 to 20% of the total weight of the composition.

In one embodiment a coating or ink composition contains the pearlescent pigment. In another embodiment an article comprises the pearlescent pigment. A coating, ink, or article may further comprise a binder, wherein the pigment represents about 0.5% to about 99.5% of the composition, about 0.1% to about 70%, or about 0.2% to about 10%.

The coating or ink may be printing ink, surface coating, coatings for laser marking, pigment preparation, dry preparation, food colorant, textile coating, architectural coating, synthetic fiber, or fiber based product. A coating may be applied to an object as a liquid, vapor, or solid. Examples of methods for applying a coating are by printing, painting, polymeric coating, or spraying. The coating may be a powder, enamel, aerosol, paint, epoxy, or polymer.

The arts of making coatings and inks, as well the various printing processes (i.e., intaglio, flexo, screen, offset, gravure) are very well known in the literatures, so it is not repeated here [see "The Printing Ink Manual", 5$^{th}$ edition, R. H. Leach, ed. Taylor & Francis, Inc.]. Other less common printing processes include digital offset solutions such as the Hewlett-Packard Indigo presses.

The ink may be a magnetic toner. An example of a magnetic toner is one that is used for Magnetic Ink Character Recognition (MICR). These toners may be used to print security codes on checks and are read by low-cost readers. Many of the toners used for MICR are black. The color and magnetic susceptibility of the MICR ink may be adjusted by using different pearlescent pigments.

Besides the topical applications such as printings or coatings, the pigments can be incorporated directly into substrates during the formation stage to make an article. For example, to a papers, the pigments can be introduced along with other regular paper fillers such as calcite, talc during paper making to fill the open pores of paper near the surface. If the article is a plastic, the pigment can be introduced during the extrusion of substrate. Examples of articles are plastic, glass, ceramic material, concrete, pressed wood, pills, paper, toothpaste, food products, or agricultural products.

The terms goniochromatic, iridescent, and pearlescent, may be used interchangeably to mean a change of color depending on the viewing angle.

Unless otherwise specified, the alkaline stability of a pigment is measured as ΔE* measured against a white background, using the procedure described in Example 32.

Unless otherwise specified, the acid stability of a pigment is measured as ΔE* measured against a white background, using the procedure described in Example 33.

Unless otherwise specified, the HPI, CIELAB coordinates, hue angle, $h_{ab}$, $L^*$, $a^*$, $b^*$, and chroma of a pigment are measured using the pigment drawdown described in Example 32 with a white or black background using a D65 illuminant and a 10 degree observer.

A homogeneous coating of a pigment is a coating that only contains one colored element, it is not a blend of colored elements. An example of a pigment that will not form a homogeneous coating is Cloisonné® Nu Antique Gold pigment, the pigment contains both color pigment and iron oxide.

EXAMPLES

Example 1

FeCl$_3$-Urea Homogenous Hydrolysis Process for Depositing an Easily Reducible FeOOH Layer A 0.1M HCl solution (356.9 g) was added to a 500 ml cylindrical reaction vessel blade (for gentle stirring and non-sticking property). The solution was stirred at 175 RPM. A 7.1 g 45% wt FeCl$_3$ Stock Solution (Riedel 12322, 45% wt FeCl$_3$, 55% water) was add drop-wise into the reactor.

Urea (16 g) was added slowly into reactor under agitation.

Sky Chemical Russet Pigment (20 g) was added to the reactor, and stirred for 5 minutes.

The temperature was increased 2° C./min to 80° C. and held for 4 hour.

The pigment is recovered by filtration and washed with distilled water.

Example 2

Solid-on-Solid Catalytic Aqueous-Phase Hydrogenation Process

Step 1—Wet Micronization of Catalyst

Platinum oxide powder (200 mg, 10-50 micron grade, Aldrich 206032) was stirred in 100 g PEG 400 (i.e., 2 mg PtO2/g fluid).

The slurry was loaded into a Eiger-Mill equipment with 0.5 mm zirconia media and water cooling jacket. The power was set to maximum and ran for 6 hours. The final slurry was a greenish black and did not settle for about 1 to 2 days.

The particle size was checked with dynamic light scattering (Horiba DLLS Particle Sizer) and OM (optical microscope, Nikon) to ensure no particles larger than 1 micron were left.

Step 2—Hydrogenation

PEG 400 (100 g), FeOOH (20 g) coated red pearl pigment (i.e., Sky Chemical Super Russet) and 3 g of the micronized PtO$_2$ slurry (2 mg catalyst/g fluid) from step 1, was loaded into a steel-constructed hydrogenation chamber.

An agitator was lowered into the chamber. The chamber was closed and connected to the H$_2$ reservoir.

The gas line was purged several times with N$_2$.

The chamber was pressurized with H$_2$ to roughly 10-14 bar.

The agitator was turned on and the heating mantle was set to 200° C. The reaction was run for 6 hours.

The heating mantle was removed to let the chamber cool. The chamber head space and lines were purged with N$_2$ gas to remove any residual H$_2$.

The chamber was opened and the slurry was poured out into a container.

Step 3—Catalyst Recovery and Pigment Wash

The slurry was settled in the container. The pearl pigment will sink to the bottom much faster than colloidal PtO$_2$. As soon as the majority of the pigment settled, the supernatant was decanted, which was rich in PtO$_2$, and put aside for reuse.

The settled pigments were then washed several times with water and one time with industrial alcohol on a mesh filter (20 micron mesh) to remove the PEG and residual colloidal PtO$_2$.

The pigment was dried under mild vacuum.

Example 3

Preparation of Homogenous Platinum Colloidal Nanoparticle Catalyst

Polyvinylpyrrolidone (PVP) Reductant Solution: Anhydrous ethylene glycol (80 g) and K15 PVP (10 g, Fluka 81390 or ISP) were mixed at 3000 RPM with a Hauschild mixer until dissolved. The mixture was added to a 1 L 3.5" Teflon Coated Cylindrical reactor with a 2" PTFE coated 3-leaf blade, and a nitrogen purging line.

Precursor Solution: Anhydrous ethylene glycol (80 g) and H$_2$PtCl$_6$-6H$_2$O salt (0.5 g, SA C3044) were added to a 4 oz jar with a magnetic stir bar, and stirred until dissolved. The liquid was sonicated for 10 minutes to remove oxygen then added to the PVP reductant solution.

Mixing of Precursor and Reductant: Anhydrous ethylene glycol (80 g) was added to the reaction vessel, followed by agitation at roughly 200 RPM to gently mix precursor with reductant at room temperature. The N$_2$ purging line was lowered to just below the liquid surface to provide an insert gas blanket.

Thermal Activation: The mixture was heated from approximately 20° C. to 120° C. in roughly 100 minutes. The mixture was held at 120° C. for 1 hour before switching off the heat. The solution was allowed to cool in the oil bath back to room temperature.

Recovery: The Pt-in-(PVP+EG) liquid [0.75 mg Pt/q-fluid] was poured into a glass jar and the jar was sealed.

Example 4

Liquid-Phase Hydrogenation Process with a Homogenous Catalyst

Step 1—Hydrogenation

PEG 400 (100 g), FeOOH coated red pearl pigment (20 g, i.e., Sky Chemical Super Russet), and Pt colloidal solution (8 g) from Example 3 (300 ppm level of Pt, normalized to dry content of pigment) was loaded into a steel-constructed hydrogenation chamber.

An agitator was lowered into the chamber. The chamber was closed and connected to the H$_2$ reservoir.

The gas line was purged several times with N$_2$.

The chamber was pressurized with H$_2$ to roughly 10-14 bar.

The agitator was turned on and the heating mantle was set to 200° C. The reaction was run for 6 hours.

The heating mantle was removed to let the chamber cool. The chamber head space and lines were purged with N$_2$ gas to remove any residual H$_2$.

The chamber was opened and the slurry was pour out into a container.

Step 2—Catalyst Recovery and Pigment Wash

After the slurry was allowed to settle in a container, the supernatant fluid was discarded.

The settle pigments were then washed several times with 10% PVP in water and one time with industrial alcohol on a mesh filter (20 micron mesh) to remove PEG and residual colloidal Pt.

The pigment was dried under mild vacuum

Example 5

Onyx Black Pearlescent Pigment

Step 1—FeOOH Deposition by $FeCl_3$-Urea Homogenous Hydrolysis

A 0.1M HCl solution (10,707 g) was added to a 15 L cylindrical reaction vessel. The solution was stirred at 175 RPM. A 213 g $FeCl_3$ Stock Solution (Riedel 12322, 45% wt $FeCl_3$, 55% water) was added drop-wise into the reactor.

Urea (1440 g) was added slowly into reactor under agitation.

Sudarshan Russet Pigment (600 g) was added to the reactor, and stirred for 5 minutes. This deposition technique is not exclusive to the Sudarshan Russet pigment. Other platelet-like substrates may be used including those comprising synthetic mica (uncoated or metal oxide coated) or flaky glass supports. These substrates may contain multiple adsorbed layers, such as those that contain materials of varying refractive index. It is important to note that equivalent levels of Fe uptake (g Fe/g mica) can be achieved using both pre-coated or uncoated supports by either redeposition or by adjustment of the reaction conditions.

The reaction temperature was increased 2° C./min to 90° C. and held for 4 hour.

The coated pigment was then recovered by vacuum filtration using a 10 micron filter. The filter cake was washed three times with 5 L of water. The coated pigment was then dried at 60° C. overnight.

Step 2—Hydrogenation

PEG 400 (1920 g), FeOOH coated red pearl pigment (400 g, i.e., Sudarshan Russet), and Pt colloidal solution (80 g) from Example 3 was loaded into a steel-constructed hydrogenation chamber.

An agitator was lowered into the chamber. The chamber was closed and connected to the $H_2$ reservoir.

The gas line was purged several times with $N_2$.

The chamber was pressurized with $H_2$ to roughly 340-380 psig.

The agitator was turned on and the heating mantle was set to 200° C. The reaction was run for 6 hours.

The heating mantle was then removed to let the chamber cool. The chamber head space and lines were purged with $N_2$ gas to remove any residual $H_2$.

The chamber was opened and the slurry was poured out into a container.

The hydrogenated pigment was then recovered by vacuum filtration using a 10 micron filter. The filter cake was washed with 4 L of water followed by 2 L of ethanol.

The pigment was then placed in an oven at 60° C. for 24 hours.

Step 3—Pigment Drawdown Preparation

The hydrogenated pigment (0.5 g) was dispersed in 4.5 g of PPG Delstar PMR499 acrylic enamel in a max 15 translucent jar designed for the DAC150FVZ-K model (Hauschild Engineering) high speed mixer.

Glass beads (2 g) were added to the dispersed suspension.

The pigment suspension (10% pigment) was then mixed for 3 minutes at 3000 rpm using a DAC150FVZ-K model high speed mixer.

Three preparations of the same 10% pigment suspension were prepared using the procedure described above. Directly following mixing, each pigment suspension was applied to a Form 2C Leneta card using either a 1.5, 3 or 6 mil Bird applicator.

Each drawdown was allowed to dry at room temperature for 30 minutes and then placed in an oven at 60° C. for an additional 30 minutes.

The colorimetric parameters (CIE $L^*a^*b^*$) of the dried films were measured using a 10 degree observer and D65 illuminant (specular component included and specular component excluded) against both a white and black reference background. The results of these measurements are listed in the tables below.

TABLE 1

Colorimetric parameters (CIE $L^*a^*b^*$) of Onyx black (Example 5) drawdowns (10% pigment) using a 10 degree observer and D65 illuminant with specular component included (SCI) at varying film thickness with a black background reference.

| Thickness | Sample Over Black Background | | | | | Uncoated Black Background | | | | |
|---|---|---|---|---|---|---|---|---|---|---|
| | L* | a* | b* | C* | H | L* | a* | b* | C* | h |
| 1.5 mil | 29.34 | 1.01 | −1.82 | 2.08 | 299.03 | 27.32 | 0.32 | −0.01 | 0.32 | 357.88 |
| 3.0 mil | 29.75 | 1.58 | −2.16 | 2.68 | 306.14 | 27.40 | 0.35 | −0.07 | 0.35 | 349.26 |
| 6.0 mil | 28.89 | 1.29 | −2.03 | 2.41 | 302.5 | 27.19 | 0.27 | −0.19 | 0.33 | 325.25 |

TABLE 2

Colorimetric parameters (CIE $L^*a^*b^*$) of Onyx black (Example 5) drawdowns (10% pigment) using a 10 degree observer and D65 illuminant with specular component included (SCI) at varying film thickness with a white background reference.

| Thickness | Sample Over White Background | | | | | Uncoated White Background | | | | |
|---|---|---|---|---|---|---|---|---|---|---|
| | L* | a* | b* | C* | H | L* | a* | b* | C* | h |
| 1.5 mil | 43.14 | 1.21 | −0.70 | 1.40 | 329.97 | 93.36 | −0.80 | 3.23 | 3.33 | 103.89 |
| 3.0 mil | 30.87 | 1.57 | −1.89 | 2.46 | 309.78 | 93.41 | −0.77 | 3.18 | 3.27 | 103.64 |
| 6.0 mil | 28.88 | 1.27 | −2.03 | 2.39 | 301.93 | 93.44 | −0.63 | 3.33 | 3.39 | 100.76 |

TABLE 3

Colorimetric parameters (CIE L*a*b*) of Onyx black (Example 5) drawdowns (10% pigment) using a 10 degree observer and D65 illuminant with specular component excluded (SCE) at varying film thickness with a black background reference.

| Thickness | Sample Over Black Background | | | | | Uncoated Black Background | | | | |
|---|---|---|---|---|---|---|---|---|---|---|
| | L* | a* | b* | C* | H | L* | a* | b* | C* | h |
| 1.5 mil | 11.17 | 1.71 | −2.48 | 3.01 | 304.59 | 8.15 | 1.03 | 1.85 | 2.12 | 60.92 |
| 3.0 mil | 13.89 | 2.82 | −2.94 | 4.07 | 313.8 | 7.90 | 1.17 | 2.15 | 2.45 | 61.59 |
| 6.0 mil | 14.88 | 2.27 | −2.62 | 3.46 | 310.90 | 8.12 | 0.93 | 1.72 | 1.95 | 61.62 |

TABLE 4

Colorimetric parameters (CIE L*a*b*) of Onyx black (Example 5) drawdowns (10% pigment) using a 10 degree observer and D65 illuminant with specular component excluded (SCE) at varying film thickness with a white background reference.

| Thickness | Sample Over White Background | | | | | Uncoated White Background | | | | |
|---|---|---|---|---|---|---|---|---|---|---|
| | L* | a* | b* | C* | H | L* | a* | b* | C* | h |
| 1.5 mil | 36.28 | 1.02 | 0.09 | 1.02 | 4.79 | 91.74 | −0.80 | 3.30 | 3.39 | 103.65 |
| 3.0 mil | 16.84 | 2.61 | −2.28 | 3.47 | 318.85 | 91.58 | −0.77 | 3.33 | 3.42 | 103.07 |
| 6.0 mil | 15.14 | 2.36 | −2.70 | 3.59 | 311.05 | 91.69 | −0.75 | 3.26 | 3.34 | 103.03 |

Example 6

Neon Green-Gold Pearlescent Pigment

A mixture of HCl (706.2 g of 0.1 M solution), FeCl$_3$ (14.2 g of 45 wt % solution), urea (96 g), and TiO$_2$ coated natural mica pigment (40 g, SunPearl Iridescent Green, 10-60 μm particle size) was charged into a 1 L jacketed pot reactor under agitation at 180 rpm. The mixture had a pH of approximately 1.8. The mixture was then heated to 90° C. The pigment is complete when urea decomposition resulted in a rise of the solution pH to between about 6.3 and 6.5. After about 2 hours at 90° C., the pigment was filtered, rinsed with deionized water, and dried at 60-80° C. A neon-like lustrous pigment having a green interference color combined with a golden yellow absorbance color was obtained. The resulting pigment contained approximately 6.5 wt % elemental iron as measured using a Perkin Elmer 5100 PC Atomic Absorption Spectrophotometer. CIELAB values measured for this pigment and the starting substrate with a Spectraflash SF600 Plus spectrophotometer are listed in Table 5.

Example 7

Neon Gold Pearlescent Pigment

A neon gold pearlescent pigments was prepared via the same technique demonstrated in Example 1, except the amount of each reagent initially charged to the reaction vessel is different as depicted in Table 6. As shown in Table 6, the amount of FeCl$_3$ used for coating was twice that used in Example 1 with the same Urea/Fe molar ratio of 40.6 and the same starting substrate. Following filtration, washing, and drying, a neon-like lustrous pigment having a golden interference color was obtained (see Table 5 for CIELAB values). The resulting pigment contained approximately 10.7 wt % elemental iron.

This example illustrates thicker coatings of FeOOH layers on TiO$_2$-coated platelet-like substrates can be utilized to progress the interference color to the next shade. This is evident by comparison of the hue angle measured over a black background (see Table 5) for the coated substrates and the starting material. The uncoated substrate has a green interference color with a hue angle of 205.1. FeOOH coating progresses the hue angle clockwise with increasing thickness. As shown for a reaction Fe/pigment mass ratio of 0.055 (or 6.5 wt % Fe in the final pigment), the hue angle progresses from a green interference color (hue angle=205.1) to a green-gold interference color (hue angle=108.6). At about double the reaction Fe/pigment mass ratio (which results in 10.7 wt % Fe in the final pigment), the hue angle further progresses to a more golden interference color (hue angle=83.0).

Increased FeOOH deposition results in a darkening of the substrate, or a drop in the L* value, as shown in Table 5. The L* value of the starting material with both white and black backgrounds is reduced as the Fe/pigment mass ratio used in deposition is increased.

TABLE 5

CIE Lab values measured for Examples 6 and 7 using a 10° observer and D65 illuminant with specular component included.

| Example | Reaction Fe/Pigment Ratio (g/g) | Final Interference Color | White Background | | | | | Black Background | | | | |
|---|---|---|---|---|---|---|---|---|---|---|---|---|
| | | | L* value | a* value | b* value | Chroma | Hue Angle | L* value | a* value | b* value | Chroma | Hue Angle |
| SunPearl Iridescent Green | 0 | Transparent Green | 92.8 | −2.3 | 5.6 | 6.0 | 112.5 | 79.9 | −12.7 | −6.0 | 14.0 | 205.1 |

TABLE 5-continued

CIE Lab values measured for Examples 6 and 7 using a 10° observer and D65 illuminant with specular component included.

| Example | Reaction Fe/Pigment Ratio (g/g) | Final Interference Color | White Background | | | | | Black Background | | | | |
|---|---|---|---|---|---|---|---|---|---|---|---|---|
| | | | L* value | a* value | b* value | Chroma | Hue Angle | L* value | a* value | b* value | Chroma | Hue Angle |
| 6 | 0.055 | Transparent Green/Gold | 78.2 | 3.7 | 35.5 | 35.5 | 84.1 | 72.8 | −9.2 | 27.5 | 29.0 | 108.6 |
| 7 | 0.110 | Transparent Gold | 74.7 | 12.4 | 46.9 | 48.5 | 75.2 | 68.4 | 4.7 | 38.3 | 38.6 | 83.0 |

Pigment drawdowns (3 mil Bird applicator) were prepared by dispersing 0.75 g pigment in 5 g of vehicle (10% CAB 531-1 (Eastman Chemical) in n-butyl acetate).

TABLE 6

Quantity of reagents used for Fe(OH)$_3$ deposition on commercially-available TiO$_2$-coated natural mica substrates.

| | | Initial Reaction Solution Composition | | | |
|---|---|---|---|---|---|
| Example | Substrate Brand Name | Pigment (g) | 45 wt % FeCl$_3$ (g) | Urea (g) | 0.1M HCl (g) |
| 6 | SunPearl Iridescent Green | 40 | 14.2 | 96 | 706.2 |
| 7 | SunPearl Iridescent Green | 40 | 28.4 | 192 | 706.2 |
| 10 | SunPearl Iridescent Gold | 40 | 14.2 | 96 | 706.2 |
| 11 | SunPearl Iridescent Gold | 40 | 28.4 | 192 | 706.2 |
| 14 | SunPearl Iridescent Red | 40 | 3.55 | 24 | 706.2 |
| 15 | SunPearl Iridescent Red | 40 | 7.1 | 48 | 706.2 |
| 16 | SunPearl Iridescent Red | 40 | 14.2 | 96 | 706.2 |
| 20 | SunPearl Iridescent Violet | 40 | 14.2 | 48 | 706.2 |
| 21 | SunPearl Iridescent Violet | 40 | 28.4 | 192 | 706.2 |
| 24 | SunPearl Iridescent Blue | 40 | 14.2 | 48 | 706.2 |
| 25 | SunPearl Iridescent Blue | 40 | 28.4 | 192 | 706.2 |

Example 8

Lustrous, Semi-Opaque Green Pearlescent Pigment

The pigment prepared in Example 6 (20 g, Mica+TiO$_2$+Fe(OH)$_3$, particle size of 10-60 μm) and PVP stabilized Pt catalyst (4 g) in ethylene glycol (prepared in Example 3) were dispersed in polyethylene glycol 400 (96 g, PEG 400, EMD Chemical, CAS 25322-68-3), and added to a 600 mL steel Parr reactor equipped with twin 45 degree pitch blade impellers. The mixture was agitated at approximately 800 rpm. The reaction solution was purged several times by pressurizing the vessel with nitrogen and then evacuating under vacuum. Following sufficient purging, the mixture was heated to 220° C., pressurized with hydrogen to 10.3 bar and held at these conditions for 6 hours. The pigment was filtered, rinsed with 4 L deionized water followed by 1 L ethanol, and dried at 60-80° C. A deep and intensely colored, semi-opaque, green pearlescent pigment (see Table 7 for corresponding CIE Lab color values) was obtained.

The weight fraction of Fe(II) and Fe(III) in the final pigment is given in Table 8. Total iron and Fe(II) content was determined via atomic absorption spectroscopy and oxidation/reduction titration with 0.1 N potassium dichromate, respectively. The hydrogenation resulted in reduction of approximately 15.4% of the deposited iron (Fe(III) to Fe(II)).

As shown in Table 7, this reduction process transformed the bichroic starting material (Example 6) into a more opaque pigment with more uniform color coordinates as measured with white and black backgrounds. The level of opacity, or hiding power can be described using a hiding power index (HPI) defined as:

$$HPI = \frac{1}{|L^*(\text{black}) - L^*(\text{white})|} \quad (3)$$

where L*(black) and L*(white) are the measured lightness or L* value on a black and white background, respectively. Full opacity is obtained when L*(black) is equivalent to L*(white) causing the hiding power index to equate to infinity. The HPI associated with this pigment is listed in Table 7.

TABLE 7

CIE Lab values measured for Examples 8 and 9 using a 10° observer and D65 illuminant with specular component included.

| Example | Reaction Fe/Pigment Ratio (g/g) | Final Interference Color | HPI | White Background | | | | | Black Background | | | | |
|---|---|---|---|---|---|---|---|---|---|---|---|---|---|
| | | | | L* value | a* value | b* value | Chroma | Hue Angle | L* value | a* value | b* value | Chroma | Hue Angle |
| SunPearl Iridescent Green | 0 | Transparent Green | 0.078 | 92.8 | −2.3 | 5.6 | 6.0 | 112.5 | 79.9 | −12.7 | −6.0 | 14.0 | 205.1 |
| 8 | 0.055 | Semi-Opaque Green | 1.56 | 61.9 | −10.2 | 20.1 | 22.6 | 116.8 | 61.3 | −11.7 | 19.4 | 22.6 | 121.1 |
| 9 | 0.110 | Opaque Gold | 50.0 | 48.3 | 5.8 | 22.8 | 23.5 | 75.7 | 48.3 | 5.6 | 22.7 | 23.4 | 76.0 |

Pigment drawdowns (3 mil Bird applicator) were prepared by dispersing 0.75 g pigment in 5 g of vehicle (10% CAB 531-1 (Eastman Chemical) in n-butyl acetate).

TABLE 8

Total composition of Fe(II) and Fe(III) measured for Examples 8 and 9.

| Example | Total Fe (g/g) | Fe(II) (g/g) | Fe(III) (g/g) | Fe(II)/Total Fe (g/g) | Fe(III)/Total Fe (g/g) |
|---|---|---|---|---|---|
| 4 | 0.065 | 0.01 | 0.055 | 0.15 | 0.85 |
| 5 | 0.107 | 0.017 | 0.09 | 0.16 | 0.84 |

Example 9

Lustrous, Opaque Gold Pearlescent Pigment

An intensely colored, gold pearlescent pigments with increased opacity relative to Example 8, was prepared according to the procedure for Example 8 except that the Fe/Pigment mass ratio used in deposition was increased by two-fold resulting in higher weight fraction of Fe in the final pigment (see Tables 7 and 8). As shown by the CIELAB values listed in Table 7, a vibrantly colored gold pearlescent pigment was obtained following hydrogenation. The resulting pigment has higher opacity, or higher hiding power index relative to Example 8 (50.0 compared to 1.56 for Example 3) as shown in Table 7.

The progression of the interference color of $TiO_2$-coated platelet like substrates and the opacity may be precisely controlled by the Fe/pigment mass ratio. As will be shown in the following examples, the two-step process (coating and reduction) may be applied to $TiO_2$ coated mica pigments with various interference colors such as: gold, red, violet, blue, green, and silver. An infinite number of lustrous, colored pearlescent pigments that span all four quadrants of the CIELAB color coordinate system may be produced while controlling the opacity to suit the intended application.

The color and opacity is directly controlled by the thickness of both the initial $TiO_2$ and the deposited FeOOH layers. For semi-opaque shades (as described in Example 8), the reduction of thin FeOOH layers result in pigments characterized by a simple progression of the initial interference color or hue angle as shown in Table 7. Reduction of thicker FeOOH layers results in further advancement of the interference color or hue angle and can progress the interference color to the next shade (in the case of Example 5, from green to yellow) while increasing the opacity or HPI.

Examples 10 Through 13

Development of Lustrous, Pearlescent Pigments Using $TiO_2$-Coated Mica with a Gold Interference Color The methods described above may be applied to $TiO_2$-coated mica substrates characterized by a yellow or gold interference color. Examples 10 and 11 are analogous to 6 and 7, except that that the substrate material used was SunPearl Iridescent Gold (10-60 µm) rather than SunPearl Iridescent Green. The composition of the reaction solution for both Example 10 and 11 is shown in Table 6 with the CIELAB values of the resulting pigments given in Table 9.

As shown previously, FeOOH deposition results in clockwise advancement of the hue angle (over a black background) of the starting substrate (see Table 9). The initial gold interference color (hue angle=93.4) is advanced to orange gold (Example 6, hue angle=68.6) at low Fe loading and further to pink (hue angle=24.2) at increased FeOOH layer thickness. Following deposition, these pigments are goniochromatic, or characterized by a specific interference color (in this case, orange, gold, or pink) at some viewing angles, with a gold to yellow absorbance color at others. The gold to yellow absorbance color is due to the precipitated yellow iron oxide or FeOOH layer. As the FeOOH thickness increases, the darkness of the coated pigment increases as shown by the measured L* values depicted in Table 9.

The reduction of Examples 10 and 11 by the hydrogenation method described in Example 8, yielded Examples 12 and 13, respectively. Example 12 is a lustrous semi-opaque, orange pigment with a HPI of 0.267. Due to the relatively thin FeOOH layer, reduction resulted in a small advancement of the hue angle, shifting the interference color from gold to orange. Although the conditions for reduction between Examples 12 and 13 were equivalent, Example 13 yields a more opaque (HPI=1.099), darker, lustrous plum pigment. The larger color shift, from a hue angle of 49.2 (Example 12 on a black background) to 354.7 (Example 13 on a black background), and the increase in opacity is due to the increased thickness of the coated FeOOH layer.

TABLE 9

CIE Lab values measured for Examples 10-13 using a 10° observer and D65 illuminant with specular component included.

| Example | Reaction Fe/Pigment Ratio (g/g) | Final Interference Color | HPI | White Background | | | | | Black Background | | | | |
|---|---|---|---|---|---|---|---|---|---|---|---|---|---|
| | | | | L* value | a* value | b* value | Chroma | Hue Angle | L* value | a* value | b* value | Chroma | Hue Angle |
| SunPearl Iridescent Gold | 0 | Transparent Gold | 0.094 | 93.3 | −1.3 | 9.6 | 9.69 | 97.9 | 82.59 | −1.0 | 17.6 | 17.6 | 93.4 |
| 10 | 0.055 | Transparent Orange-Gold | 0.118 | 76.8 | 16.2 | 46.8 | 49.6 | 70.9 | 68.4 | 14.3 | 36.4 | 39.1 | 68.6 |
| 11 | 0.110 | Transparent Pink | 0.091 | 67.0 | 26.7 | 29.1 | 39.5 | 47.5 | 56.0 | 24.2 | 10.9 | 26.5 | 24.2 |
| 12 | 0.055 | Semi-Opaque Orange | 0.267 | 59.6 | 28.9 | 34.8 | 45.2 | 50.3 | 55.9 | 25.6 | 29.7 | 39.2 | 49.2 |
| 13 | 0.110 | Semi-Opaque Plum | 1.099 | 37.9 | 15.6 | −0.5 | 15.6 | 358.0 | 37.0 | 14.9 | −1.4 | 15.0 | 354.7 |

Pigment drawdowns (3 mil Bird applicator) were prepared by dispersing 0.75 g pigment in 5 g of vehicle (10% CAB 531-1 (Eastman Chemical) in n-butyl acetate).

Examples 14 Through 19

Development of Lustrous, Pearlescent Pigments Using TiO$_2$-Coated Mica with a Red Interference Color Examples 14 through 19 were prepared according to the procedure described in Example 6, except that the TiO$_2$-coated mica substrates (SunPearl Iridescent Red, 10-60 μm) were characterized by a pink to red interference color. The reaction Fe/Pigment mass ratios used are indicated in Table 6. The CIELAB values for each pigment prepared are shown in Table 10.

For clarity, the a* and b* coordinates of Examples 14-16 measured against a black background are plotted in FIG. 1. Pigment drawdowns (3 mil Bird applicator) of Examples 14-16 were prepared by dispersing 0.75 g pigment in 5 g of vehicle (10% CAB 531-1 (Eastman Chemical) in n-butyl acetate). FIG. 1 shows that deposition at very low Fe/pigment ratios, in particular for Fe/pigment ratios less than about 0.055, results in an initial increase in the b* coordinate with small impact on the a* value. This is perhaps due to the characteristic yellow absorbance of FeOOH. It is from this point, point 2 in FIG. 1, that the clockwise shift in hue angle begins at increasing FeOOH layer thickness. As shown, the hue angle begins to progress pass the initial hue angle of the support material at Fe/pigment ratios of about 0.055. For Example 16 (Fe/pigment ratio=0.055), the interference color is noticeably violet indicating sufficient progression to the next shade (red to violet).

The reduction of Examples 14-16 by the hydrogenation method described in Example 8, yielded Examples 17-19, respectively. As shown by the CIELAB values depicted in Table 10, reduction yields lustrous, pearlescent pigments ranging from pink to light violet, and the hiding power index, or HPI, associated with these pigments increased with increasing Fe/pigment mass ratio.

TABLE 10

CIE Lab values measured for Examples 14-19 using a 10° observer and D65 illuminant with specular component included.

| Example | Reaction Fe/Pigment Ratio (g/g) | Final Interference Color | HPI | White Background | | | | | Black Background | | | | |
| --- | --- | --- | --- | --- | --- | --- | --- | --- | --- | --- | --- | --- | --- |
| | | | | L* value | a* value | b* value | Chroma | Hue Angle | L* value | a* value | b* value | Chroma | Hue Angle |
| SunPearl Iridescent Red | 0 | Transparent Pink/Red | 0.047 | 91.9 | 1.14 | 4.36 | 4.51 | 75.3 | 70.7 | 17.3 | −6.6 | 18.5 | 339.3 |
| 14 | 0.01375 | Transparent Pink | 0.069 | 83.2 | 11.9 | 21.6 | 24.7 | 61.2 | 68.8 | 17.3 | 3.0 | 17.5 | 9.8 |
| 15 | 0.0275 | Transparent Pink | 0.073 | 79.4 | 17.0 | 21.1 | 27.1 | 51.0 | 65.7 | 18.7 | 1.6 | 18.8 | 4.8 |
| 16 | 0.055 | Transparent Pink-Violet | 0.059 | 70.7 | 23.1 | 12.7 | 26.4 | 28.8 | 53.7 | 19.1 | −14.5 | 24.0 | 322.8 |
| 17 | 0.01375 | Transparent Pink | 0.068 | 72.6 | 23 | 15.3 | 27.6 | 33.6 | 58.0 | 26.2 | −4.9 | 26.6 | 349.4 |
| 18 | 0.0275 | Transparent Pink | 0.095 | 63.4 | 31.5 | 9.5 | 32.9 | 16.8 | 52.9 | 27.8 | −6.9 | 28.7 | 346.2 |
| 19 | 0.055 | Semi-Opaque Light Violet | 0.305 | 47.7 | 18.2 | −12.9 | 22.3 | 324.6 | 44.4 | 18.4 | −17.4 | 25.3 | 316.6 |

Pigment drawdowns (3 mil Bird applicator) were prepared by dispersing 0.75 g pigment in 5 g of vehicle (10% CAB 531-1 (Eastman Chemical) in n-butyl acetate).

Examples 20 Through 23

Development of Lustrous, Pearlescent Pigments Using TiO$_2$-Coated Mica with a Violet Interference Color Examples 20 and 21 were prepared according to the procedure described in Example 6, except the TiO$_2$-coated mica substrate had a violet interference color (SunPearl Iridescent Violet, 10-60 μm), and used reaction Fe/pigment ratios of 0.055 and 0.110, respectively as shown in Table 6. The CIELAB values for the pigments following FeOOH deposition are given in Table 11.

TABLE 11

CIE Lab values measured for Examples 20-23 using a 10° observer and D65 illuminant with specular component included.

| Example | Reaction Fe/Pigment Ratio (g/g) | Final Interference Color | HPI | White Background | | | | | Black Background | | | | |
| --- | --- | --- | --- | --- | --- | --- | --- | --- | --- | --- | --- | --- |
| | | | | L* value | a* value | b* value | Chroma | Hue Angle | L* value | a* value | b* value | Chroma | Hue Angle |
| SunPearl Iridescent Violet | 0 | Transparent Violet | 0.047 | 91.2 | 1.4 | 2.5 | 2.9 | 60.2 | 69.7 | 17.7 | −16.7 | 24.3 | 316.7 |

TABLE 11-continued

CIE Lab values measured for Examples 20-23 using a 10° observer and D65 illuminant with specular component included.

| Example | Reaction Fe/Pigment Ratio (g/g) | Final Interference Color | HPI | White Background L* value | a* value | b* value | Chroma | Hue Angle | Black Background L* value | a* value | b* value | Chroma | Hue Angle |
|---|---|---|---|---|---|---|---|---|---|---|---|---|---|
| 20 | 0.055 | Transparent Violet | 0.064 | 74.9 | 16.7 | 12.6 | 20.9 | 37.07 | 59.3 | 6.1 | −13.1 | 14.5 | 295.0 |
| 21 | 0.110 | Transparent Blue | 0.096 | 72.8 | 8.6 | 21.6 | 23.3 | 68.4 | 62.4 | −11.4 | 4.3 | 12.2 | 159.4 |
| 22 | 0.055 | Semi-Opaque Dark Violet | 0.532 | 44.2 | 3.9 | −21.1 | 21.5 | 280.4 | 42.3 | 2.0 | −23.9 | 24.0 | 274.8 |
| 23 | 0.110 | Opaque Dark Blue | 4.762 | 43.5 | −10.4 | −5.5 | 11.8 | 208.0 | 43.3 | −10.8 | −6.04 | 12.4 | 209.24 |

Pigment drawdowns (3 mil Bird applicator) were prepared by dispersing 0.75 g pigment in 5 g of vehicle (10% CAB 531-1 (Eastman Chemical) in n-butyl acetate).

The pigments of Examples 20 and 21 displayed the characteristic clockwise shift in hue angle, resulting in the gradual progression from a violet to blue interference color at increased Fe/pigment ratio. The reduction of Examples 20 and 21, using the conditions described in Example 8, yielded Examples 22 and 23, respectively. As shown in Table 11, the reduction of thin FeOOH surface layers (such as Example 22) yields a semi-opaque pearlescent pigment characterized by a color similar to the interference color of the $TiO_2$-coated mica support. In this case, Example 22 yields a lustrous, dark violet pearlescent pigment. Reduction of thicker FeOOH layers, such as the pigment produced in Example 23, results in an advancement of the interference color to the next shade (in this case from violet to blue) and increased opacity or HPI.

Examples 24 Through 27

Development of Lustrous, Pearlescent Pigments Using $TiO_2$-Coated Mica with a Blue Interference Color Examples 24 and 25 were prepared according to the procedure described in Example 6, except the $TiO_2$-coated mica substrate had a blue interference color (SunPearl Iridescent Blue, 10-60 μm), and used reaction Fe/pigment ratios of 0.055 and 0.110, respectively, as shown in Table 6. The CIELAB values are given in Table 12.

The pigments of Examples 24 and 25 displayed the characteristic clockwise shift in hue angle resulting in the gradual progression from a blue to green interference color at increased Fe/pigment ratio. The reduction of Examples 24 and 25, using the conditions described in Example 6 yielded Examples 26 and 27, respectively. As shown in Table 12, the reduction of thin FeOOH surface layers (such as Example 26) yields a semi-opaque pearlescent pigment characterized by a color similar to the interference color of the $TiO_2$-coated mica support. In this case, Example 26 yields a lustrous, turquoise pearlescent pigment. Reduction of thicker FeOOH layers, such as the pigment produced in Example 27, results in an advancement of the interference color to the next shade (in this case from an iridescent blue to opaque olive green) and increased opacity or HPI.

The examples described above indicate that an almost infinite number of lustrous, vibrant colored pearlescent shades with controlled opacity may be prepared by the methods described herein. The potential color range spans the CIELAB color space.

TABLE 12

CIELAB values measured for Examples 24-27 using a 10° observer and D65 illuminant with specular component included.

| Example | Reaction Fe/Pigment Ratio (g/g) | Final Interference Color | HPI | White Background L* value | a* value | b* value | Chroma | Hue Angle | Black Background L* value | a* value | b* value | Chroma | Hue Angle |
|---|---|---|---|---|---|---|---|---|---|---|---|---|---|
| SunPearl Iridescent Blue | 0 | Transparent Blue | 0.053 | 92.2 | −1.0 | 0.9 | 1.3 | 137.5 | 73.2 | −7.1 | −22.5 | 23.6 | 252.5 |
| 24 | 0.055 | Transparent Blue | 0.103 | 76.7 | 5.9 | 15.7 | 16.8 | 69.37 | 67.0 | −15.8 | −0.2 | 15.8 | 180.6 |
| 25 | 0.110 | Transparent Green Gold | 0.173 | 71.4 | 5.6 | 35.3 | 35.7 | 81.1 | 65.6 | −9.51 | 25.9 | 27.6 | 110.2 |
| 26 | 0.055 | Semi-Opaque Turquoise | 0.520 | 60.3 | −8.5 | 1.2 | 8.6 | 171.7 | 58.4 | −17.0 | −3.4 | 17.4 | 191.3 |
| 27 | 0.110 | Opaque Olive Green | 2.170 | 49.5 | −9.9 | 13.4 | 16.6 | 126.4 | 49.1 | −10.1 | 12.8 | 16.3 | 128.4 |

Pigment drawdowns (3 mil Bird applicator) were prepared by dispersing 0.75 g pigment in 5 g of vehicle (10% CAB 531-1 (Eastman Chemical) in n-butyl acetate).

Examples 28 Through 31

Development of Lustrous, Pearlescent Pigments Using TiO$_2$-Coated Mica with a Silver Interference Color Examples 28 and 29 were prepared according to the procedure described in Example 6, except the TiO$_2$-coated mica substrate had a silver interference color (SunPearl Silver White, 10-60 μm), and used Fe/pigment ratios of 0.055 and 0.110, respectively, as shown in Table 13. The CIELAB values are given in Table 14.

TABLE 13

Quantity of reagents used for FeOOH deposition on commercially-available TiO$_2$-coated natural mica substrates.

| | | Initial Reaction Solution Composition | | |
|---|---|---|---|---|
| Example | Substrate Brand Name | Pigment (g) | 45 wt % FeCl$_3$ (g) | Urea (g) | 0.1M HCl (g) |
| 28 | SunPearl Silver White | 40 | 14.2 | 96 | 706.2 |
| 29 | SunPearl Silver White | 40 | 28.4 | 192 | 706.2 |

TABLE 14

CIELAB values measured for Examples 28-31 using a 10° observer and D65 illuminant with specular component included.

| | | | | White Background | | | | | Black Background | | | | |
|---|---|---|---|---|---|---|---|---|---|---|---|---|---|
| Example | Reaction Fe/Pigment Ratio (g/g) | Final Interference Color | HPI | L* value | a* value | b* value | Chroma | Hue Angle | L* value | a* value | b* value | Chroma | Hue Angle |
| SunPearl Silver White | 0 | Transparent Silver | 0.136 | 93.0 | −0.1 | 3.6 | 3.6 | 91.2 | 85.6 | −1.5 | −2.4 | 2.9 | 237.8 |
| 28 | 0.055 | Transparent Gold-Silver | 0.232 | 85.4 | 6.3 | 21.5 | 22.4 | 73.6 | 81.0 | 0.6 | 14.7 | 14.7 | 87.8 |
| 29 | 0.110 | Transparent Gold | 0.376 | 78.1 | 8.8 | 28.5 | 29.8 | 72.9 | 75.5 | 3.9 | 24.6 | 25.0 | 81.1 |
| 30 | 0.055 | Semi-Opaque Champagne | 0.862 | 76.7 | 6.4 | 21.7 | 22.6 | 73.5 | 75.6 | 4.4 | 19.9 | 20.4 | 77.5 |
| 31 | 0.110 | Opaque Metallic Grey | 1.852 | 61.9 | 1.8 | 12.6 | 12.8 | 81.9 | 61.4 | 1.5 | 12.2 | 12.3 | 83.11 |

Pigment drawdowns (3 mil Bird applicator) were prepared by dispersing 0.75 g of pigment in 5 g of vehicle (10% CAB 531-1 (Eastman Chemical) in n-butyl acetate).

As shown in Table 14, FeOOH deposition results in a transition from a transparent silver white to golden shades. The deposition of thicker FeOOH layers results in a more golden color and a noticeably darker appearance (lower L* value). The reduction of Examples 28 and 29, using the conditions described in Example 8 yielded Examples 30 and 31, respectively. Example 30 is a lustrous, semi-opaque, champagne-colored pearlescent pigment with a HPI of 0.862. At increased reaction Fe/pigment mass ratio, as used in Example 31, gave a more opaque (HPI=1.852), metallic grey pearlescent pigment with a darker appearance (lower L* value, see Table 14).

Example 32

Alkaline Stability Testing—Blue Pearlescent Pigments

Example 23 and six commercially available blue pearlescent pigments were tested for alkaline stability. The samples tested and their corresponding components are listed in Table 15.

TABLE 15

Pigment samples tested for alkaline (pH 12.5) stability.

| Sample | Supplier | Product Code | Composition | Particle Size Range (μm) |
|---|---|---|---|---|
| Example 23 | Sun Chemical | | Mica, TiO$_2$, Fe$_3$O$_4$ | 10-60 |
| Duocrome ® BY | Engelhard | 226C | Mica, TiO$_2$, Iron Blue | 6-50 |
| Duocrome ® BR | Engelhard | 426C | Mica, TiO$_2$, Iron Blue | 6-50 |
| Duocrome ® BV | Engelhard | 526C | Mica, TiO$_2$, Iron Blue | 6-50 |
| Duocrome ® BG | Engelhard | 826C | Mica, TiO$_2$, Iron Blue | 6-50 |
| Cosmica ® Blue | Engelhard | MCB27 | Mica, Iron Blue | 6-48 |
| Cloisonné ® Blue | Engelhard | 626C | Mica, TiO$_2$, Iron Blue | 6-48 |

A basic solution (pH 12.5, NaOH in distilled water) was mixed with 2 wt % pigment (see Table 15) to prepare suspensions. The suspensions were mixed, and allowed to settle for about 5 hours. The pigments were then filtered, rinsed with deionized water, and dried at 80° C.

Pigment drawdowns (3 mil Bird applicator) were prepared by dispersing 0.5 g of each pigment in 4.5 g of vehicle (PPG Delstar DMR499 Acrylic Enamel), followed by applying the mixture to a Leneta Form 2C opacity card. The CIELAB color coordinates (10° observer and D65 illuminant with specular component included) for the treated and untreated samples were measured using a Spectraflash SF600 Plus spectrophotometer at a 90° viewing angle. The hiding power index (before and after treatment) and color difference or ΔE* ($\Delta E^* = ((\Delta L^*)^2 + (\Delta a^*)^2 + (\Delta b^*)^2)^{1/2}$) between the treated and untreated samples were measured against a black and white background, see Table 16.

TABLE 16

Hiding power index (HPI) and color difference values (ΔE*) for blue pearlescent pigment samples before and after alkaline treatment (pH 12.5, 5 hours).

| | | | ΔE* (Treated vs Untreated) | |
|---|---|---|---|---|
| Sample | HPI (Untreated) | HPI (Treated) | White Background | Black Background |
| Example 23 | 0.469 | 0.408 | 1.71 | 1.40 |
| Duocrome ® BY | 0.294 | 0.068 | 39.66 | 21.82 |
| Duocrome ® BR | 0.110 | 0.036 | 46.01 | 15.29 |
| Duocrome ® BV | 0.091 | 0.033 | 50.75 | 13.26 |
| Duocrome ® BG | 0.315 | 0.063 | 45.99 | 20.84 |
| Cosmica ® Blue | 0.649 | 0.119 | 14.23 | 2.79 |
| Cloisonné ® Blue | 0.169 | 0.039 | 56.50 | 16.94 |

All the commercially available blue pearlescent pigments tested displayed a marked shift in color and opacity following immersion in alkaline solution. The measured color difference is due to the instability of iron blue in alkaline environment. The absence of iron blue or ferric ferrocyanide in the preparation of blue pearlescent pigments represents a significant advantage in terms of alkaline stability. For the blue pearlescent pigment prepared as described in Example 23, the treated and untreated samples showed a small relative color difference (ΔE*<2) with a marginal drop in opacity (HPI drop from 0.469 to 0.408).

Example 33

Acid Stability Testing—Red/Pink Pearlescent Pigments

Example 18 and six commercially available red/pink mica based pearlescent pigments were tested for acid stability. The samples tested and their corresponding components are listed in Table 17.

TABLE 17

Pigment samples tested for acid (pH 1.5) stability.

| Sample | Supplier | Product Code | Composition | Particle Size Range (μm) |
|---|---|---|---|---|
| Example 18 | Sun Chemical | | Mica, TiO$_2$, Fe$_3$O$_4$ | 10-60 |
| Duocrome ® RY | Engelhard | 224C | Mica, TiO$_2$, Carmine | 6-50 |
| Duocrome ® RO | Engelhard | 324C | Mica, TiO$_2$, Carmine | 6-50 |
| Duocrome ® RV | Engelhard | 524C | Mica, TiO$_2$, Carmine | 6-50 |
| Gemtone ® Ruby | Engelhard | G010 | Mica, TiO$_2$, Iron Oxide, Carmine | 6-48 |
| Cloisonné ® Red | Engelhard | 424C | Mica, TiO$_2$, Carmine | 6-48 |
| Cloisonné ® Nu Antique Red | Engelhard | 424CB | Mica, TiO$_2$, Iron Oxides, Carmine | 6-48 |
| Cosmica ® Red | Engelhard | MCNR4 | Mica, Carmine | 6-48 |

An acidic solution (pH 1.5 of concentrated HCl in distilled water) was mixed with 2 wt % pigment (see Table 17) to prepare a suspension. The suspensions were mixed, and allowed to settle for about 20 hours. The pigments were filtered, rinsed with deionized water and dried at 80° C.

Drawdown preparation and color analysis was performed as described in the previous example. The hiding power index (before and after treatment) and color difference or ΔE* between the treated and untreated samples measured against a black and white background is shown in Table 18.

As shown in Table 18, the pink pearlescent pigment of Example 18 showed the lowest color difference (or lower ΔE*) against a white background following exposure to acidic conditions. Only the Cosmica® Red showed lower ΔE* measured against a black background. This low value of ΔE* measured for the Cosmica® Red sample is due to the similarity of its L* value (L*=27.25) with that of the black background (L*=27.20) as shown in Table 19. In reality, the Cosmica® Red sample showed significant degradation as is evident by its marked change in color coordinates measured against a white background as depicted in Table 20 (ΔE*=16.258).

TABLE 18

Hiding power index (HPI) and color difference values (ΔE*) for red pearlescent pigment samples before and after acid treatment (pH 1.5, 20 hours).

| | | | ΔE* (Treated vs Untreated) | |
|---|---|---|---|---|
| Sample | HPI (Untreated) | HPI (Treated) | White Background | Black Background |
| Example 18 | 0.063 | 0.058 | 3.024 | 1.589 |
| Duocrome ® RY | 0.159 | 0.120 | 12.068 | 7.944 |
| Duocrome ® RO | 0.098 | 0.069 | 17.154 | 7.753 |
| Duocrome ® RV | 0.060 | 0.047 | 17.615 | 5.524 |
| Gemtone ® Ruby | 0.254 | 0.225 | 3.935 | 2.609 |
| Cloisonné ® Red | 0.077 | 0.061 | 15.263 | 6.402 |
| Cloisonné ® Nu Antique Red | 1.111 | 0.546 | 3.311 | 2.097 |
| Cosmica ® Red | 0.066 | 0.035 | 16.258 | 1.432 |

TABLE 19

CIE Lab values measured against a black background using a 10° observer and D65 illuminant with specular component included.

| | Untreated Pigment | | | | | Treated Pigment (pH 1.5, 20 hr) | | | | |
|---|---|---|---|---|---|---|---|---|---|---|
| Sample | L* value | a* value | b* value | Chroma | Hue angle | L* value | a* value | b* value | Chroma | Hue angle |
| Example 18 | 45.80 | 23.5 | -9.39 | 25.31 | 338.22 | 46.45 | 24.54 | -8.38 | 25.94 | 341.15 |
| Duocrome ® RY | 64.52 | 9.67 | 16.08 | 18.76 | 58.99 | 68.58 | 4.1 | 20.03 | 20.45 | 78.43 |
| Duocrome ® RO | 56.84 | 19.45 | 10.75 | 22.23 | 28.93 | 60.79 | 14.3 | 14.99 | 20.71 | 46.35 |

TABLE 19-continued

CIE Lab values measured against a black background using a 10° observer and D65 illuminant with specular component included.

| Sample | Untreated Pigment | | | | | Treated Pigment (pH 1.5, 20 hr) | | | | |
|---|---|---|---|---|---|---|---|---|---|---|
| | $L^*$ value | $a^*$ value | $b^*$ value | Chroma | Hue angle | $L^*$ value | $a^*$ value | $b^*$ value | Chroma | Hue angle |
| Duocrome ® RV | 46.73 | 24.7 | −30.39 | 39.17 | 309.11 | 49.61 | 21.08 | −27.37 | 34.55 | 307.61 |
| Gemtone ® Ruby | 45.79 | 29.83 | 0.00 | 29.83 | 360 | 47.42 | 28.35 | 1.4 | 28.38 | 2.83 |
| Cloisonné ® Red | 49.2 | 29.66 | −10.24 | 31.38 | 340.96 | 52.74 | 26.01 | −6.35 | 26.78 | 346.29 |
| Cloisonné ® Nu Antique Red | 35.83 | 14.82 | −6.35 | 16.12 | 336.78 | 37.53 | 14.45 | −5.18 | 15.35 | 340.28 |
| Cosmica ® Red | 27.25 | 4.14 | 0.97 | 4.25 | 13.19 | 27.08 | 3.11 | −0.01 | 3.11 | 359.74 |

Pigment drawdowns (3 mil Bird applicator) were prepared by dispersing 0.5 g pigment in 4.5 g of vehicle (PPG Delstar DMR499 Acrylic Enamel).

In addition to improved color consistency in the dry form, the pigment of Example 18 was the only sample that showed no signs of colorant bleeding into the acidic solution. Following filtration of the acidic suspensions, the filtrate was analyzed in the visible region for colorant bleeding (see FIG. 2). As shown in FIG. 2, the pigment prepared by the current invention was the only filtrate sample that showed no significant absorption in the visible region. All acidic suspensions containing commercial pigments were red in appearance indicative of the instability of carmine colorants in acidic environments.

TABLE 20

CIE Lab values measured against a white background using a 10° observer and D65 illuminant with specular component included.

| Sample | Untreated Pigment | | | | | Treated Pigment (pH 1.5, 20 hr) | | | | |
|---|---|---|---|---|---|---|---|---|---|---|
| | $L^*$ value | $a^*$ value | $b^*$ value | Chroma | Hue angle | $L^*$ value | $a^*$ value | $b^*$ value | Chroma | Hue angle |
| Example 18 | 61.58 | 29.44 | 14.81 | 32.95 | 26.7 | 63.62 | 29.33 | 17.04 | 33.92 | 30.16 |
| Duocrome ® RY | 70.81 | 20.76 | 9.54 | 22.85 | 24.69 | 76.88 | 11.65 | 14.62 | 18.69 | 51.46 |
| Duocrome ® RO | 67.01 | 28.73 | 4.68 | 29.11 | 9.25 | 75.25 | 15.81 | 12.39 | 20.09 | 38.09 |
| Duocrome ® RV | 63.3 | 33.47 | −13.04 | 35.92 | 338.72 | 71.02 | 21.26 | −2.96 | 21.47 | 352.07 |
| Gemtone ® Ruby | 49.72 | 35.65 | 4.98 | 36 | 7.94 | 51.87 | 33.32 | 7.31 | 34.11 | 12.37 |
| Cloisonné ® Red | 62.18 | 36.82 | −4.23 | 37.06 | 353.45 | 69.17 | 25.95 | 3.89 | 26.24 | 8.52 |
| Cloisonné ® Nu Antique Red | 36.73 | 15 | −6.11 | 16.2 | 337.83 | 39.36 | 13.88 | −4.44 | 14.57 | 342.26 |
| Cosmica ® Red | 42.47 | 47.18 | 2.3 | 47.23 | 2.8 | 55.75 | 38.07 | 0.07 | 38.07 | 0.11 |

Pigment drawdowns (3 mil Bird applicator) were prepared by dispersing 0.5 g pigment in 4.5 g of vehicle (PPG Delstar DMR499 Acrylic Enamel).

Example 34

Alkaline Stability Testing—Green Pearlescent Pigments

Example 27 and three commercially available green mica based pearlescent pigments were tested for alkaline stability. The samples tested and their corresponding components are listed in Table 21.

TABLE 21

Pigment samples tested for alkaline (pH 12.5) stability.

| Sample | Supplier | Product Code | Composition | Particle Size Range (μm) |
|---|---|---|---|---|
| Example 27 | Sun Chemical | | Mica, $TiO_2$, $Fe_3O_4$ | 10-60 |
| Cloisonné Green | Engelhard | 828C | Mica, $TiO_2$, $Cr_2O_3$ | 6-48 |
| Cloisonné Blue Green | Engelhard | 728C | Mica, $TiO_2$, $Cr_2O_3$ | 6-48 |
| Cloisonné Nu Antique Green | Engelhard | 828CB | Mica, $TiO_2$, $Cr_2O_3$, Iron Oxides | 6-48 |

A basic solution (pH 12.5, NaOH in distilled water) was mixed with 2 wt % pigment (see Table 21) to prepare suspensions. The suspensions were mixed, and allowed to settle for about 55 hours. The pigments were then filtered, rinsed with deionized water, and dried at 80° C.

Drawdown preparation and color analysis was performed as described in Example 32. The hiding power index (before and after treatment) and color difference or $\Delta E^*$ between the treated and untreated samples measured against a black and white background is shown in Table 22.

TABLE 22

Hiding power index (HPI) and color difference values ($\Delta E^*$) for green pearlescent pigment samples before and after alkaline treatment (pH 12.5, 55 hours).

| Sample | HPI (Untreated) | HPI (Treated) | $\Delta E^*$ (Treated vs Untreated) White Background | Black Background |
|---|---|---|---|---|
| Example 27 | 0.505 | 0.417 | 2.49 | 1.78 |
| Cloisonné Green | 0.099 | 0.107 | 0.36 | 0.64 |
| Cloisonné Blue Green | 0.099 | 0.087 | 1.64 | 0.69 |
| Cloisonné Nu Antique Green | 1.351 | 0.329 | 16.68 | 14.14 |

Table 21 consists of three types of green pearlescent pigments: Mica-TiO$_2$+Cr$_2$O$_3$ (Cloisonné Green and Blue Green), Mica-TiO$_2$+Cr$_2$O$_3$ mixed with iron oxide particles (Cloisonné Nu Antique Green) and Example 27. A difference between the pigment of Example 27 and the commercially available green pearlescent pigments shown in Table 21 is the absence of Cr$_2$O$_3$. Freedom from chromium containing compounds allows for the use of these green pearlescent pigments in more cosmetic compositions, specifically in applications involving the lip area.

As shown in Table 22, the color stability in alkaline environments of the green pearlescent pigment ($\Delta E^*$=2.49 over a white background and $\Delta E^*$=1.78 over a black background) described in example 27 is consistent with values observed for the blue pearlescent pigment ($\Delta E^*$=1.71 over a white background and $\Delta E^*$=1.40 over a black background) described in examples 23 and 32.

In addition to being chromium-free, the green pearlescent pigments described may be made in both transparent (low HPI) and opaque (high HPI) varieties. TiO$_2$-coated mica pigments containing a layer of Cr$_2$O$_3$ are generally restricted to transparent pearlescent pigments as depicted in Table 22 (HPI=0.099). On the other hand, Example 27 is much more opaque (HPI=0.505) than both the Cloisonné Green and Blue Green. This is significant when considering that the particle size distribution for Example 27 is slightly higher (see Table 21) than the Cloisonné series pigments. This property allows a more lustrous, green pearlescent pigment with improved hiding power or opacity compared to Cr$_2$O$_3$ coated mica-based pigments.

In order to improve hiding power or opacity, conventional Cr$_2$O$_3$ coated mica-based pigments can be combined with loose iron oxide particles to create opaque green pearlescent pigments, such as the technique used to prepare Cloisonné Nu Antique Green (see Table 21). As shown in Table 22, this results in a significant increase in hiding power or surface coverage (HPI=1.351). However, a significant drawback of this approach is the loss of luster due to excess light scattering and the general dirty appearance that results from the presence of these loose nonplatelet-like particles. This approach also results in a significant loss of color stability in liquid preparations (as depicted by the high $\Delta E^*$ shown in Table 22) due to separation of the loose iron oxide particles from the Cr$_2$O$_3$ coated mica-based pigment.

Example 35

Semi Transparent, Carmine-Free, Red Pearlescent Pigments

Five carmine-free and seven carmine containing red pearlescent pigments were compared, see Table 23. The color of the drawdown of the pigments were red, and had a hue angle from not less than about 275 to not more than about 50 degrees. Drawdown preparation and color analysis was performed as described in example 32. The CIELAB color coordinates and the hiding power index for each sample is depicted in Table 24. The pearlescent pigment of example 18 was the only red pearlescent pigment that does not contained carmine with a HPI less than about 1.

TABLE 23

Red Pearlescent Pigments

| Sample | Pigment | Supplier | Contains Carmine |
|---|---|---|---|
| 1 | Example 18 | SunChemical | N |
| 2 | Duocrome ® RY | Engelhard/BASF | Y |
| 3 | Duocrome ® RO | Engelhard/BASF | Y |
| 4 | Duocrome ® RV | Engelhard/BASF | Y |
| 5 | Gemtone ® Ruby | Engelhard/BASF | Y |
| 6 | Cloisonné ® Red | Engelhard/BASF | Y |
| 7 | Cloisonné ® Nu Antique Red | Engelhard/BASF | Y |
| 8 | Cosmica ® Red | Engelhard/BASF | Y |
| 9 | Xirona ® Le Rouge | Merck | N |
| 10 | Sunshine Super Russet | SunChemical | N |
| 11 | SunPearl Maroon | SunChemical | N |
| 12 | SunPearl Bronze | SunChemical | N |

TABLE 24

HPI of Red Pearlescent Pigments

| | | White Background | | | | | Black Background | | | | |
|---|---|---|---|---|---|---|---|---|---|---|---|
| Sample | HPI | L* value | a* value | b* value | Chroma | Hue angle | L* value | a* value | b* value | Chroma | hue angle |
| 1 | 0.063 | 61.58 | 29.44 | 14.81 | 32.95 | 26.7 | 45.8 | 23.5 | −9.39 | 25.31 | 338.22 |
| 2 | 0.159 | 70.81 | 20.76 | 9.54 | 22.85 | 24.69 | 64.52 | 9.67 | 16.08 | 18.76 | 58.99 |
| 3 | 0.098 | 67.01 | 28.73 | 4.68 | 29.11 | 9.25 | 56.84 | 19.45 | 10.75 | 22.23 | 28.93 |
| 4 | 0.060 | 63.3 | 33.47 | −13.04 | 35.92 | 338.72 | 46.73 | 24.7 | −30.39 | 39.17 | 309.11 |
| 5 | 0.254 | 49.72 | 35.65 | 4.98 | 36 | 7.94 | 45.79 | 29.83 | 0 | 29.83 | 360 |
| 6 | 0.077 | 62.18 | 36.82 | −4.23 | 37.06 | 353.45 | 49.2 | 29.66 | −10.24 | 31.38 | 340.96 |
| 7 | 1.111 | 36.73 | 15 | −6.11 | 16.2 | 337.83 | 35.83 | 14.82 | −6.35 | 16.12 | 336.78 |

TABLE 24-continued

HPI of Red Pearlescent Pigments

| | | White Background | | | | | Black Background | | | | |
|---|---|---|---|---|---|---|---|---|---|---|---|
| Sample | HPI | L* value | a* value | b* value | Chroma | Hue angle | L* value | a* value | b* value | Chroma | hue angle |
| 8 | 0.066 | 42.47 | 47.18 | 2.3 | 47.23 | 2.8 | 27.25 | 4.14 | 0.97 | 4.25 | 13.19 |
| 9 | 2.564 | 44.73 | 40.17 | 19.61 | 44.7 | 26.01 | 44.34 | 39.48 | 19.04 | 43.83 | 25.74 |
| 10 | 1.613 | 46.02 | 31.33 | 12.63 | 33.78 | 21.96 | 45.4 | 29.5 | 11.4 | 31.63 | 21.12 |
| 11 | 1.099 | 45.61 | 32.23 | 16.17 | 36.06 | 26.64 | 44.7 | 29.79 | 14.54 | 33.15 | 26.02 |
| 12 | 3.704 | 61.98 | 18.38 | 27.52 | 33.09 | 56.26 | 61.71 | 16.95 | 26.98 | 31.86 | 57.86 |

Example 36

Clear Gel Lip Gloss Preparation

The constituents of the clear gel lip gloss base shown in Table 25 are mixed homogeneously and heated to 80° C. Following sufficient cooling to room temperature, the pigment from Example 8 was added at 2 wt % to the base gel and mixed thoroughly. Similar lip gloss preparations used pigments from Examples 18, 19, 23, 24, 25, 27 and 31.

TABLE 25

Composition of clear gel lip gloss base.

| Ingredients | Weight Fraction (%) |
|---|---|
| Versagel ME750 (Penreco) | 81.5 |
| Ceraphyl 368 (Sblack, ISP) | 10 |
| Ceraphyl 55 (ISP) | 5 |
| Isostearyl Isostearate (Mosselman) | 3 |
| Germaben (Clariant) | 0.5 |

Prophetic Example 47

Nail Varnish

The cosmetic composition of a nail lacquer comprising a pearlescent pigment may be prepared from the components set forth in the Table below.

| Components | Amount (%) |
|---|---|
| Nail polish base (Kirker Enterprises, Inc. of Patterson, NJ) | 94 |
| pearlescent pigment | 6 |
| Total | 100 |

Prophetic Example 48

Lipstick

The cosmetic composition of a lipstick comprising a pearlescent pigment may be prepared from the components set forth in the Table below.

| Components | Amount (g) |
|---|---|
| Octyldodecyl ricinoleate | 10.2 |
| Castor oil | 18 |
| Tridecyl trimellitate | 3 |
| Octyldodecanol | 4 |
| Tridecyl trimellitate | 3 |
| Lanolin wax | 6 |
| Lanolin oil | 6 |
| Hydrogenated cocoglycerides | 5 |
| Acetylated lanolin | 3 |
| Hydrogenated milk glycerides | 5 |
| Pentaerythritylk tetraisononanoate | 4 |
| Ozokerite wax | 5 |
| Candelilla wax | 5 |
| Carnauba wax | 1 |
| Synthetic wax | 3 |
| Butylated hydroxyanisole | 0.5 |
| Propylparaben | 0.15 |
| FD&C Yellow 6 (1:2 aluminum lake castor oil dispersion) | 7.5 |
| Black iron oxide castor oil dispersion (1:2) | 0.6 |
| Red iron castor oil dispersion (1:2) | 2 |
| pearlescent pigment | 8 |
| Total | 99.95 |

Prophetic Example 49

Lip Gloss

The cosmetic composition of a lip gloss comprising a pearlescent pigment may be prepared from the components set forth in the Table below.

| Components | Amount (g) |
|---|---|
| Hydroxystearic acid | 1.46 |
| Trimethylolpropane triisostearate | 10.93 |
| Polybutene | 59 |
| Mineral oil | 5.37 |
| Isocetyl stearate | 8.02 |
| Diisostearyl malate | 8.38 |
| FD&C Blue 1 (aluminum lake) | 0.01 |
| D&C Red 7 (calcium lake) | 0.02 |
| Polyethylene tetrephthalate | 0.2 |
| pearlescent pigment | 8 |
| Total | 101.39 |

Prophetic Example 50

Mascara

The cosmetic composition of a mascara comprising a pearlescent pigment may be prepared from the components set forth in the Table below.

| Components | Amount (g) |
| --- | --- |
| Petroleum Distillate | 68 |
| Polyethylene | 12 |
| Dihydroabietyl alcohol | 5 |
| Candelilla wax | 2.4 |
| Aluminum stearate | 0.05 |
| Butylparaben | 0.1 |
| Black iron oxide | 4 |
| pearlescent pigment | 8 |
| Total | 99.55 |

Prophetic Example 51

Face Powder

The cosmetic composition of a face powder comprising a pearlescent pigment may be prepared from the components set forth in the Table below.

| Components | Amount (g) |
| --- | --- |
| Iron oxide | 6.57 |
| Zinc stearate | 4 |
| Titanium dioxide | 2 |
| Bismuth oxychloride | 10 |
| Nylon powder sold under the name "ORGASOL ®" by the company ATOCHEM | 20 |
| Vaseline oil | 3.26 |
| Oleyl alcohol | 0.6 |
| Isopropyl myristate | 0.43 |
| Propyl para-hydroxybenzoate | 0.12 |
| pearlescent pigment | 3 |
| Talc qs. | 100 |
| Total | 149.98 |

Prophetic Example 52

Eye Shadow

The cosmetic composition of a eye shadow comprising a pearlescent pigment may be prepared from the components set forth in the Table below.

| Components | Amount (%) |
| --- | --- |
| Talc | 49.75 |
| Titanium dioxide | 1 |
| Zinc stearate | 5 |
| Red iron oxide | 0.15 |
| Yellow iron oxide | 0.1 |
| Polyethylene | 3 |
| Magnanese violet | 5 |
| Iridescent red nacreous | 25 |
| Mineral oil | 7 |
| Dimethicone fluid | 4 |
| Total | 100 |

Prophetic Example 53

Blush

The cosmetic composition of a blush comprising a pearlescent pigment may be prepared from the components set forth in the Table below.

| Components | Amount (g) |
| --- | --- |
| Zinc stearate | 3 |
| Titanium oxide | 2 |
| Iron oxide | 9 |
| Mica | 24 |
| Nylon powder sold under the name ORGASO ® by the company ATOCHEM | 15 |
| pearlescent pigment | 5 |
| Vaseline oil | 3.26 |
| Oleyl alcohol | 0.6 |
| Isopropyl myristate | 0.43 |
| Propyl para-hydroxybenzoate | 0.12 |
| Talc qs. | 100 |
| Total | 162.41 |

Prophetic Example 54

Hair and Body Gel

The cosmetic composition of a hair and body gel comprising a pearlescent pigment may be prepared from the components set forth in the Table below.

| Components | Amount (%) |
| --- | --- |
| Deionized water | 84 |
| Carbomer | 2 |
| pearlescent pigment | 7.8 |
| Glycerin | 2.5 |
| Vinylpyrrolidone/vinyl actetate copolymer | 2.5 |
| Triethanolamine | 1 |
| Germaben-11 ® | 0.2 |
| Total | 100 |

Prophetic Example 55

Lotion

The cosmetic composition of a lotion comprising a pearlescent pigment may be prepared from the components set forth in the Table below.

| Components | Amount (g) |
|---|---|
| Deionized water | 79.6 |
| Carbomer | 0.5 |
| Polysorbate | 0.8 |
| Propylene glycol | 2 |
| Glycerin | 5 |
| Triethanolamine | 0.6 |
| pearlescent pigment | 2 |
| Acetylated lanolin alcohol | 3 |
| Cetyl alcohol | 2 |
| Stearic acid | 5 |
| LiquaPar ® | 0.5 |
| Total | 101 |

Prophetic Example 56

Foundation

The cosmetic composition of a lipstick comprising a pearlescent pigment may be prepared from the components set forth in the Table below.

| Components | Amount (g) |
|---|---|
| Glycerol stearate | 2.2 |
| Triglycerides of capric/caprylic acids sold under the name "MIGLYOL 812 ®" by the company DYNAMIT NOBEL | 15.0 |
| Yellow iron oxides | 0.75 |
| Brown iron oxides | 0.47 |
| Black iron oxide | 0.23 |
| Titanium dioxide | 4.55 |
| Methyl para-hydroxybenzoate | 0.1 |
| Propyl para-hydroxybenzoate | 0.1 |
| Imidazolidinyl urea | 0.3 |
| 2-hydroxy-4-methoxybenzophenone | 0.5 |
| Octyl N,N-dimethylparaaminobenzoate. | 0.5 |
| Pearlescent pigment | 3.0 |
| Aluminum and magnesium silicate sold under the name "VEEGUM ®" by the company VENDERBILT | 1.0 |
| Triethanolamine | 1.0 |
| Cellulose gum | 0.16 |
| Aluminum salt of the product of the reaction of octenylsuccinic anhydride with starch sold under the name "DRY FLO ®" by the company NATIONAL STARCH | 5.0 |
| Cyclomethicone sold under the name "VOLATIL SILICONE 7158 ®" by the company UNION CARBIDE | 10.0 |
| Water | 47.34 |
| Propylene glycol | 2.0 |
| Glycerin | 3.0 |
| Sodium salt of lauroylsarcosine sold under the name "ORAMIX L30 ®" by the company SEPPIC | 0.6 |
| Stearic acid | 2.2 |
| Total | 100 |

Example 57

Eye Shadow Cream

| Ingredient | wt % |
|---|---|
| Phase A | |
| Water | (q.s to 100%) 64.20% |
| Magnesium Aluminum Silicate | 1.00% |
| Xanthan Gum | 0.30% |
| Phase B | |
| Triethanolamine (TEA 99%) | 0.30% |
| Propylene Glycol | 8.00% |
| Preservative (Water soluble) | q.s. |
| Phase C | |
| Pearlescent pigment | 20.00% |
| Phase D | |
| Stearic Acid (Stearic Acid 94%) | 4.00% |
| Glyceril Stearate | 0.80% |
| Oleyl Alcohol | 0.50% |

Procedure:

Xanthan gum and magnesium aluminum silicate were dispersed into deionized water using high shear mixing until the mixture was smooth, to form Phase A. Triethanolamine, propylene glycol, and a water soluble preservative were added to the smooth gum mixture of Phase A and mixed until smooth. Stearic acid, glyceril stearate, and oleyl alcohol were heated to 75±5° C. with gentle agitation, to form Phase D.

The pearlescent pigment material was added to the Phase A-B mixture with gentle agitation, and maintained at a temperature of 75±5° C. Phase D was added to the Phase A-BC mixture with gentle agitation, while maintaining a temperature of 75±5° C. A constant agitation was maintained and the overall mixture was cooled to 35±5° C.

When the Eye Shadow Cream was applied on skin, the following results were observed:

| Pearlescent pigment | Result |
|---|---|
| Example 27 | shimmering Olive green shade with green and red iridescent sparkling points, depending on the viewing angle |

Example 58

Eye Shadow Gel

| Ingredient | wt % |
|---|---|
| Phase A | |
| Water | (q.s to 100%) 63.00% |
| Acrylates/C10-30 Alkyl Acrylate Crosspolymer | 0.30% |

-continued

| Ingredient | wt % |
|---|---|
| Phase B | |
| Water | 13.00% |
| Glycerin | 2.00% |
| Triethanolamine (TEA 99%) | 0.70% |
| Preservative (Water Soluble) | q.s to 100% |
| Phase C | |
| Pearlescent pigment | 20.00% |

Procedure:

Acrylates/C10-30 alkyl acrylate crosspolymer was dispersed in deionized water using high shear mixing until the mixture was smooth. Glycerin, triethanolamine, and water soluble preservative were dispersed in part of the deionized water of Phase B, then added to the mixture of Phase A, and mixed until smooth.

The pearlescent pigment material of Phase C was added to the Phase A-B mixture with gentle agitation at room temperature.

Both on the container of the eye shadow gel and when it is applied on the skin, the following results were observed:

| Pearlescent pigment | Result |
|---|---|
| Example 70 | sparkling deep and warm brilliant black shade with russet and multi-iridescent white, gold, red, violet, blue and green sparkling points, depending on the viewing angle, with a vinyl effect |
| Example 25 | sparkling metallic gold shade with green iridescent duocrome effect and small red, green and turquoise sparkling points, depending on the viewing angle |

Example 59

Pressed Powder

| Ingredient | wt % |
|---|---|
| Phase A | |
| Talc | 45-80% (q.s to 100) |
| Dimethicone and Dimethicone Crosspolymer | 5.00% |
| Preservatives | (q.s to 100) |
| Phase B | |
| Pearlescent pigment | 15.00-50.00% |

Procedure:

Talc, dimethicone and dimethicone crosspolymer, and preservatives were thoroughly blended and dispersed in an appropriate dry blending/dispersing equipment. The pearlescent pigment material of Phase B was added to the dry blended ingredients and mixed until uniform.

When the opaque Pressed Powder Eye Shadow was applied onto skin, the following color travel results were observed:

| Pearlescent pigment | Result |
|---|---|
| Example 66 | shimmering old bronze-beige veil with gold, red and green sparkling points, depending on the viewing angle |

Example 60

Nail Polish

Nail Polish Base:

| Ingredient | wt % |
|---|---|
| Butyl Acetate | 25-50% |
| Ethyl Acetate | 10-25% |
| Nitrocellulose | 10-25% |
| Acetyl Tributyl Citrate | 5-10% |
| Phtalic Anhydride/Trimellitic Anhydride/Glycol Copolymer | 5-10% |
| Isopropyl Alcohol | 5-10% |
| Stearalkonium Hectorite | 1-5% |
| Adipic Acid/Fumaric Acid/Phtalic Acid/Tricyclodecane Dimethanol Copolymer | 1-5% |
| Citric Acid | <0.1% |

Procedure:

Pearlescent pigment (5 parts) was mixed with Nail Polish Base (95 parts) in an appropriate size vessel fitted with a Lightning™ type propeller mixer. The components were mixed until uniform.

The following strong color travel results, both in the clear nail enamel and in the lacquer, applied to the nail were observed:

| Pearlescent pigment | Result |
|---|---|
| Example 18 | shimmering light yellow-pink shade with red and violet iridescent sparkling points, depending on the viewing angle |
| Example 28 | shimmering silver gold shade with kind of satin effect with white, gold, red and green iridescent sparkling points, depending on the viewing angle |
| Example 31 | shimmering "old dark bronze" shade with gold, red and green iridescent sparkling points, depending on the viewing angle |

Example 60

High Gloss Colored Lipstick

| Ingredient | wt % |
|---|---|
| Phase A | |
| Castor Oil | (q.s to 100%) 14.56% |
| Isononyl Isononanoate | 17.51% |
| Pentaerythrityl TetraCaprylate/Tetracaprate | 8.75% |
| Octyldodecanol | 5.47% |
| Lanolin Oil | 11.93% |
| Caprylic/Capric/Stearic Triglyceride | 7.11% |

-continued

| Ingredient | wt % |
|---|---|
| Candelilla Wax | 9.30% |
| Carnauba Wax | 3.28% |
| Polybutene H-100 | 7.66% |
| Ozokerite | 2.20% |
| Lanolin Wax | 1.09% |
| Red 7 Lake | 0.80% |
| Preservative | q.s. |
| Antioxidant | q.s. |
| Phase B | |
| Pearlescent pigment | 10.00% |
| Phase C | |
| Fragrance | 0.10% |

Procedure:

Castor oil, isononyl isononanoate, pentaerythrityl tetracaprylate/tetracaprate, octyldodecanol, lanolin oil, caprylic/capric/stearic triglyceride, candelilla wax, carnauba wax, polybutene H-100, ozokerite, lanolin wax, red 7 lake, preservative, and antioxidant were all weighed and placed into a heated vessel. The temperature was raised to 85±3° C. The ingredients were stirred until they were melted and uniform.

The pearlescent pigment of Phase B was dispersed in the castor oil of Phase A then milled in either a colloid or roller mill. The dispersed pigment was then added and mixed with the remainder of Phase A. The fragrance of Phase C was then added and mixed with constant stirring. The composition was poured at 75±5° C. then molded, cooled, and flamed into lipstick.

The following results in the opaque High Gloss Colored Lipstick were observed:

| Pearlescent pigment | Result |
|---|---|
| Example 23 | shimmering deep red-violet shade with intense blue iridescent sparkling points, depending on the viewing angle |
| Example 8 | shimmering deep red-bronze shade with red and green iridescent sparkling points, depending on the viewing angle |

Example 61

High Gloss Lipstick

| Ingredient | wt % |
|---|---|
| Phase A | |
| Castor Oil | (q.s to 100%) 15.36% |
| Isononyl Isononanoate | 17.51% |
| Pentaerythrityl TetraCaprylate/Tetracaprate | 8.75% |
| Octyldodecanol | 5.47% |
| Lanolin Oil | 11.93% |
| Caprylic/Capric/Stearic Triglyceride | 7.11% |
| Candelilla Wax | 9.30% |
| Carnauba Wax | 3.28% |
| Polybutene H-100 | 7.66% |
| Ozokerite | 2.20% |
| Lanolin Wax | 1.09% |
| Preservative | q.s. |
| Antioxidant | q.s. |

-continued

| Ingredient | wt % |
|---|---|
| Phase B | |
| Pearlescent pigment | 10.00% |
| Phase C | |
| Fragrance | 0.10% |

Procedure:

Castor oil, isononyl isononanoate, pentaerythrityl tetracaprylate/tetracaprate, octyldodecanol, lanolin oil, caprylic/capric/stearic triglyceride, candelilla wax, carnauba wax, polybutene H-100, ozokerite, lanolin wax, preservative, and antioxidant were all weighed and placed into a heated vessel. The temperature was raised to 85±3° C. The ingredients were stirred until they were melted and uniform.

The pearlescent pigment of Phase B was dispersed in the castor oil of Phase A then milled in either a colloid or roller mill. The dispersed pigment was then added and mixed with the remainder of Phase A. Fragrance from Phase C was then added and mixed with constant stirring. The composition was poured at 75±5° C., then molded, cooled and flamed into lipstick.

The following results in the opaque High Gloss Lipstick were observed:

| Pearlescent pigment | Result |
|---|---|
| Example 24 | shimmering transparent light beige lipstick with an intense turquoise iridescent sparkling effect, depending on the viewing angle |
| Example 19 | shimmering deep violet lipstick with red, blue and violet iridescent sparkling effect, depending on the viewing angle |

Example 62

Clear Gel Lip Gloss

| Ingredient | wt % |
|---|---|
| Phase A | |
| Hydrogenated Polyisobutene and Ethylene/Propylene/Styrene Copolymer and Butylene/Ethylene/Styrene Copolymer | 73.35% |
| Ethylhexyl Palmitate | 9.00% |
| Tridecyl Neopentanoate | 4.50% |
| Isostearyl Isostearate | 2.70% |
| Preservative | q.s. |
| Phase B | |
| Ingredient | wt % |
| Pearlescent pigment | 10.00% |

Procedure:

A pearlescent pigment was prepared as described in Example 6, except that SunPearl Maroon was used in place of SunPearl Iridescent Green. The pigment was then reduced using the procedure described in Example 8 except at a temperature of 200° C. A deep and intensely colored, opaque, plum shade pearlescent pigment was obtained and used as Phase B.

Hydrogenated polyisobutene, ethylene/propylene/styrene copolymer, butylene/ethylene/styrene copolymer, ethylhexyl palmitate, tridecyl neopentanoate, isostearyl isostearate, and preservative were all weighed and placed into a heated vessel. The temperature was raised to 50±3° C. The ingredients were stirred until they were melted and uniform. At room temperature, pearlescent pigment of Phase B, was added to Phase A and mixed until all the pearlescent pigment was well dispersed. Fragrance may be added if needed, and mixed with constant stirring. The composition was poured at room temperature.

The following results in the transparent Clear Gel Lip Gloss were observed:

| Pearlescent pigment | Result |
| --- | --- |
| Phase B | intense shimmering dark plum shade vinyl effect lipgloss with red, gold green and turquoise iridescent sparkling effect, depending on the viewing angle |

Example 63

Bath and Shower Gel

| Ingredient | wt % |
| --- | --- |
| Phase A | |
| Water | (qs to 100%) 67.80 |
| Acrylates/C10-30 Alkyl Acrylate Crosspolymer | 0.70 |
| Preservatives | q.s. |
| Propylene Glycol | 1.00 |
| Pearlescent pigment | |
| Phase B | |
| TEA-Lauryl Sulfate | 23.00 |
| Cocamidopropyl Betaine | 3.50 |
| Cocamide DEA | 3.00 |
| Disodium EDTA | 0.05 |
| Phase C | |
| Fragrance | 0.20% |
| Phase D | |
| Triethanolamine | |

Procedure:

The acrylates/C10-30 alkyl acrylate crosspolymer were dispersed in water in a suitable vessel with constant agitation until uniform. The remainder of the Phase A ingredients were added to the mixture followed by heating the mixture to 65° C. The Phase B ingredients were added one at a time with constant mixing. The mixture was cooled to 40° C., and the Phase C & D ingredients were added.

The following results in the Bath and Shower Gel was observed:

| Pearlescent pigment | Result |
| --- | --- |
| Example 7 | shimmering red gold shade a bright bottle appearance with red, violet and gold iridescent sparkling effect, depending on the viewing angle |
| Example 70 | intense shimmering black bottle appearance with red, gold green to turquoise iridescent sparkling effect, depending on the viewing angle |

Example 64

Color Effect Shampoo

| Ingredients | wt % |
| --- | --- |
| Phase A | |
| Deionized Water | q.s. |
| Acrylates Copolymer (30%) | 8.00 |
| Sodium Laureth Sulfate (2 mole, 28%) | 40.0 |
| Sodium Hydroxide (18%) (q.s. to pH 6.5) | 1.50 |
| Phase B | |
| Cocamidopropyl Betaine (30%) | 6.70 |
| Polyquaternium 39 (10%) | 2.10 |
| Tetrasodium EDTA | 0.05 |
| Phenoxyethanol and Parabens | 0.50 |
| Phase C | |
| Pearlescent pigment | 0.10% |

Procedure:

Acrylates copolymer was added to deionized water, followed by sodium laureth sulfate with gentle mixing. The pH of the mixture was adjusted to 6.5 with sodium hydroxide. Ingredients of Phase B were added to the mixture in order, while mixing. The pH was adjusted to 6.5 with sodium hydroxide, if necessary. Add Phase C to the mixture with gentle stirring until homogeneous.

The following results in the Color Effect Shampoo were observed:

| Pearlescent pigment | Result |
| --- | --- |
| Example 7 | shimmering red gold shade a bright bottle appearance with red, violet and gold iridescent sparkling effect, depending on the viewing angle |
| Example 70 | intense shimmering black bottle appearance with red, gold green to turquoise iridescent sparkling effect, depending on the viewing angle |

Example 65

Color Effect Styling Gel

| Ingredient | wt % |
| --- | --- |
| Phase A | |
| Distilled Water (Aqua) | q.s. |
| Tetrasodium EDTA | 0.10 |
| DMDM Hydantoin | 0.40 |
| PEG-7M | 0.20 |

-continued

| Ingredient | wt % |
|---|---|
| Phase B | |
| Glycerin | 1.00 |
| Dimethicone Copolyol | 0.20 |
| Acrylates/Stearate-20 Itaconate Copolymer | 4.00 |
| Triethanolamine) (to pH 6.8-7.1) | 0.70 |
| Phase C | |
| PVP | 7.00 |
| Phase D | |
| Pearlescent pigment | 5.00% |

Procedure:

The ingredients of phase A were mixed in a suitable vessel. The ingredients of Phase B were added in order with mixing. After a clear gel formed, Phase C was added, followed by Phase D with stirring Maintain the agitation until homogeneous.

The following results in the Hair Styling Gel were observed:

| Pearlescent pigment | Result |
|---|---|
| Example 7 | shimmering red gold shade a bright bottle appearance with red, violet and gold iridescent sparkling effect, depending on the viewing angle |
| Example 70 | intense shimmering black bottle appearance with red, gold green to turquoise iridescent sparkling effect, depending on the viewing angle |

Example 66

Magnetic Pearlescent Pigment

SunPearl Bronze (20 g, C84-6281, SunChemical) was reduced as described in Example 8 to form a deep and intensely colored, golden-beige pearlescent pigment (see Table 7 for corresponding CIELAB color values) was obtained. The magnetic susceptibility of the resulting pigment as well as, the starting pigment were measured by Applied Paleomagnetics in Santa Cruz, Calif. using a Bartington MS2 susceptibility meter.

TABLE 26

Magnetic susceptibility of Example 66.

| Sample | Color | Magnetic Susceptibility × $10^5$ ($m^3$/kg) |
|---|---|---|
| SunPearl Bronze | Bronze | 0.019 |
| Example 66 | Golden-Beige | 5.056 |

Example 67

Particle Alignment of Example 66 Using a Magnetic Field

Pigment drawdowns of the pigment prepared in Example 66 and the starting pigment of SunPearl Bronze were prepared as described in Example 32.

Four circular button magnets (13 mm ProMAG®, Magnetic Specialty LLC, Neodymium (Grade 35, 12,300 gauss) magnet) were placed on a tray in an oven maintained at 50° C. After positioning the magnets, a 0.64 cm thick glass plate was placed directly over the magnets. Directly following application of the pigment suspensions, the opacity card is placed on the glass plate so that each circular magnet is located directly beneath the white and black background for both the starting pigment of Example 66 and the pigment prepared in Example 66. The pigment prepared in Example 66 (magnetic susceptibility=$5.056 \times 10^{-5}$ $m^3$/kg) instantaneously oriented into a three-dimensional circular pattern with unique depth of perception above both the white and black background. The starting material from Example 66, SunPearl Bronze (magnetic susceptibility=$0.019 \times 10^{-5}$ $m^3$/kg), displayed no change upon placement above the magnetic field, indicating that the mass susceptibility was too low to orient the pigment in this magnetic field. After 10-15 minutes in the oven, the three-dimensional image was cured and fixed within the coating.

The CIELAB values of the coatings were measured as described in Example 32. The aligned pigment, was measured in the center of the circular image formed by the magnet. The central portion of three-dimensional magnetic image appears black ($L^* \sim 30$) over both the white and black backgrounds. The black appearance may be due to the orientation of the platelet-like pigments normal to the surface. Alignment normal to the surface significantly reduces the area available for reflection resulting in a black appearance. The measured color difference ($\Delta E^*$) between the central portion of the circular image (maximum alignment normal to the coating surface) and the region devoid of the applied magnetic field was 25.9 and 27.2 over white and black respectively, as shown in Table 27.

TABLE 27

CIELAB Color of Magnetically Aligned Pigments

| Example | Dry Pigment Color | White Background | | | | | Black Background | | | | |
|---|---|---|---|---|---|---|---|---|---|---|---|
| | | $L^*$ value | a value | b value | Chroma | Hue Angle | $L^*$ value | a value | b value | Chroma | Hue Angle |
| SunPearl Bronze | Bronze | 63.51 | 18.61 | 28.33 | 33.9 | 56.70 | 63.1 | 17.09 | 27.78 | 32.61 | 58.39 |
| Unaligned Example 66 | Golden-Beige | 54.27 | 6.4 | 15.84 | 17.08 | 68.01 | 54.30 | 6.33 | 15.73 | 16.96 | 68.07 |
| Central Portion of 3-D Circular Image in Example 66 | Not Applicable | 30.78 | 4.22 | 5.03 | 6.57 | 50.01 | 29.99 | 2.79 | 4.08 | 4.94 | 55.61 |

Example 68

Magnetic Properties of Green Pearlescent Pigment

A pearlescent pigment is prepared as described in Example 25, forming a neon-like lustrous pigment having a green interference color combined with a golden yellow absorbance color (Example 68a). The pigment was then reduced using the procedure described in Example 27 to form an opaque olive green, lustrous pearlescent pigment (Example 68b). The magnetic susceptibility of the pigments measured before and after hydrogenation is given in Table 28. As shown, the magnetic susceptibility increased by roughly three orders of magnitude following hydrogenation.

TABLE 28

Magnetic susceptibility of Example 68.

| Sample | Dry Pigment Color | Magnetic Mass Susceptibility × $10^{-5}$ ($m^3$/kg) |
|---|---|---|
| Example 68a (Before Reduction) | Neon Green-Gold | 0.008 |
| Example 68b (After Reduction) | Olive | 7.165 |

Pigment drawdowns for both pigments were made and measured as described in Example 67. The measured color difference ($\Delta E^*$) between the central portion of the circular image (maximum alignment normal to the coating surface) and the region devoid of the applied magnetic field was 24.1 and 28.3 over white and black respectively.

TABLE 29

CIELAB Color of Magnetically Aligned Pigments

| Example | Dry Pigment Color | White Background | | | | | Black Background | | | | |
|---|---|---|---|---|---|---|---|---|---|---|---|
| | | L* value | a value | b value | Chroma | Hue Angle | L* value | a value | b value | Chroma | Hue Angle |
| Example 68a (Before Reduction) | Neon Green-Gold | 74.61 | 7.98 | 43.64 | 44.36 | 79.64 | 61.27 | −10.78 | 26.16 | 28.3 | 112.4 |
| Example 68b (After Reduction) | Olive | 49.64 | −5.58 | 18.52 | 19.35 | 106.77 | 48.18 | −7.3 | 16.93 | 18.44 | 113.33 |
| Central Portion of 3-D Circular Image in Example 4b | Not Applicable | 30.83 | 2.66 | 5.84 | 6.42 | 65.52 | 26.2 | −0.37 | 0.48 | 0.61 | 127.36 |

Example 69

Magnetic Properties of a Blue Pearlescent Pigment

A pearlescent pigment is prepared as described in Example 23, forming a semi-opaque lustrous blue pearlescent pigment with a magnetic mass susceptibility of $3.858 \times 10^{-5}$ $m^3$/kg.

Pigment drawdowns for the pigment was made and measured as described in Example 67, and shown in Table 30. The measured color difference ($\Delta E^*$) between the central portion of the circular image (maximum alignment normal to the coating surface) and the region devoid of the applied magnetic field was 21.43 and 21.33 over white and black respectively.

TABLE 30

CIELAB Color of Magnetically Aligned Pigments

| Example | Dry Pigment Color | White Background | | | | | Black Background | | | | |
|---|---|---|---|---|---|---|---|---|---|---|---|
| | | L* value | a value | b value | Chroma | Hue Angle | L* value | a value | b value | Chroma | Hue Angle |
| Example 69 (After Reduction) | Blue | 45.18 | −5.74 | −3.59 | 6.77 | 212.00 | 43.32 | −10.30 | −6.48 | 12.17 | 212.16 |

TABLE 30-continued

| | | White Background | | | | | Black Background | | | | |
|---|---|---|---|---|---|---|---|---|---|---|---|
| | Dry | | | | | | | | | | |
| Example | Pigment Color | L* value | a value | b value | Chroma | Hue Angle | L* value | a value | b value | Chroma | Hue Angle |
| Central Portion of 3-D Circular Image in Example 69 | Not Applicable | 32.65 | 7.71 | 7.42 | 10.70 | 43.91 | 25.80 | 0.33 | −0.58 | 0.67 | 299.54 |

Example 70

Preparation of a Magnetic Black Pearlescent Pigment

A pearlescent pigment is prepared as described in Example 68, except that SunPearl Maroon is used. The pigment was then reduced using the procedure described in Example 8 to form an opaque onyx black pearlescent pigment with a magnetic mass susceptibility of $14.017 \times 10^{-5}$ m$^3$/kg.

Pigment drawdowns for the pigment was made and measured as described in Example 67, and shown in Table 31. The measured color difference ($\Delta E^*$) between the central portion of the circular image (maximum alignment normal to the coating surface) and the region devoid of the applied magnetic field was 4.2 and 5.0 over white and black respectively.

TABLE 31

| | | White Background | | | | | Black Background | | | | |
|---|---|---|---|---|---|---|---|---|---|---|---|
| | Dry | | | | | | | | | | |
| Example | Pigment Color | L* value | a value | b value | Chroma | Hue Angle | L* value | a value | b value | Chroma | Hue Angle |
| Example 70 | Black | 29.37 | 1.15 | −2.22 | 2.50 | 297.35 | 29.43 | 1.07 | −2.32 | 2.56 | 294.65 |
| Central Portion of 3-D Circular Image in Example 70 | Not Applicable | 25.61 | 0.68 | −0.33 | 0.76 | 334.01 | 24.70 | 0.35 | −0.80 | 0.88 | 293.53 |

Example 71

Pearlescent Pigment in PVC

A PVC base of clear plasticol (Geon 121A, 55 parts by weight), diisodecyl phthalate plasticizer (44 parts by weight), and Mark 4152 Stabilizer (1 part by weight) were mixed until uniform. The pigment of Example 66 (1 wt % of the PVC base) was mixed with the PVC base. The uncured polymer was drawn down on a glass plate (thickness=0.32 cm) using a 6 mil Bird applicator. The glass plate was then placed on 8 circular magnets in an oven heated at 180° C. After 5 minutes, the plasticized PVC drawdown is removed from the oven and allowed to cool. The resulting plastic film has a warm beige pearlescent appearance containing three dimensional circular images with unique depth.

Example 72

Cosmetic Nail Enamel Use Application

The pigment from Example 66 was added at 4 wt % to a nail enamel base (Tevco, Product 8711) and mixed at 3000 rpm for 3 minutes using a DAC150FVZ-K model (Hauschild Engineering) high speed mixer. The nail enamel was then applied to an opacity card (Leneta Form 3B) using a 3 mil (~76 micron) Bird applicator.

Four circular button magnets (13 mm ProMAG®, Magnetic Specialty LLC) were placed on a tray in an oven maintained at 50° C. After positioning the magnets, a 0.64 cm thick glass plate was placed directly over the magnets. Directly following application of the nail enamel, the opacity card is placed on the glass plate such that two circular magnets are located directly beneath both the white and black background.

Upon placement of the card, the pigment prepared in Example 66 instantaneously oriented into a three-dimensional circular pattern with unique depth of perception above both the white and black background.

Comparative Example 73

Acrylic Enamel Coatings of Commercially Available Products

Commercially available colored pearlescent pigments were tested, for their magnetic mass susceptibility, and CIELAB color for aligned and non-aligned pigments in coatings.

TABLE 32

Mass susceptibility and composition.

| Sample | Supplier | Composition | Mass Susceptibility × $10^5$ (m$^3$/kg) |
|---|---|---|---|
| Cloisonné ® Nu Antique Gold | BASF | Mica, TiO$_2$, Fe$_3$O$_4$, Fe$_3$O$_2$ | 7.966 |
| Colorona Blackstar ® Red | Merck | Mica and Iron Oxides (CI: 77499) | 11.556 |
| Colorona Blackstar ® Blue | Merck | Mica and Iron Oxides (CI: 77499) | Not available |
| Colorona Blackstar ® Gold | Merck | Mica and Iron Oxides (CI: 77499) | 11.084 |

TABLE 32-continued

Mass susceptibility and composition.

| Sample | Supplier | Composition | Mass Susceptibility × $10^5$ (m³/kg) |
|---|---|---|---|
| Colorona Blackstar ® Green | Merck | Mica and Iron Oxides (CI: 77499) | Not available |

The drawdown procedure used in Example 67 was applied to the pigments listed in Table 32. The application of the magnetic field to the Cloisonné® Nu Antique Gold pigment did not show the dramatic platelet realignment to create the three-dimensional effect, instead the coating was only darkened. The pigment may be made from magnetic iron oxide particles that are not bound to the platelet substrate. Consequently, application of a magnetic field does not align the platelets to give the three-dimensional effect. The CIELAB values of the other coatings were measured as described in Example 67.

TABLE 33

CIELAB Color of Magnetically Aligned Pigments

| Example | Dry Pigment Color | White Background | | | | | Black Background | | | | |
|---|---|---|---|---|---|---|---|---|---|---|---|
| | | L* value | a value | b value | Chroma | Hue Angle | L* value | a value | b value | Chroma | Hue Angle |
| Colorona Blackstar ® Red (or CBR) | Black-Red | 34.50 | 9.73 | 2.14 | 9.97 | 12.42 | 34.63 | 9.65 | 1.88 | 9.84 | 11.05 |
| Central Portion of 3-D Circular Image in CBR | Not Applicable | 27.01 | 2.54 | 0.96 | 2.71 | 20.71 | 25.76 | 1.58 | 0.04 | 1.58 | 1.62 |
| Colorona Blackstar ® Blue (or CBB) | Black-Blue | 31.72 | −1.52 | −5.13 | 5.35 | 253.48 | 31.88 | −1.78 | −5.39 | 5.67 | 251.76 |
| Central Portion of 3-D Circular Image in CBB | Not Applicable | 29.86 | −0.77 | −4.11 | 4.18 | 259.34 | 30.42 | −1.31 | −4.85 | 5.03 | 254.92 |
| Colorona Blackstar ® Gold (or CBG) | Black-Gold | 44.70 | 9.91 | 18.55 | 21.04 | 61.89 | 45.17 | 10.00 | 18.88 | 21.36 | 62.09 |
| Central Portion of 3-D Circular Image in CBG | Not Applicable | 30.56 | 4.93 | 6.27 | 7.97 | 51.80 | 29.99 | 3.89 | 5.42 | 6.67 | 54.33 |
| Colorona Blackstar ® Green (or CBGr) | Black-Green | 33.66 | −4.17 | −2.29 | 4.76 | 208.75 | 33.9 | −4.39 | −2.31 | 4.96 | 207.77 |
| Central Portion of 3-D Circular Image in CBGr | Not Applicable | 25.49 | 0.09 | −1.12 | 1.13 | 274.74 | 25.51 | −0.14 | −1.28 | 1.29 | 263.59 |

Table 34 shows the measured color difference (ΔE*) between the magnetically aligned region and the region devoid of the magnetic field of the examples is higher than the color difference for commercially available pigments.

TABLE 34

The change in color difference (ΔE*) between the region devoid of the applied external magnetic field and the center portion of the aligned 3-D circular image.

| Example | Dry Pigment Color | White Background, ΔE* | Black Background, ΔE* |
|---|---|---|---|
| Example 66 | Golden-Beige | 25.94 | 27.19 |
| Example 68 | Olive Green | 24.14 | 28.31 |
| Example 69 | Blue | 21.43 | 21.33 |
| Colorona Blackstar ® Red | Black-Red | 10.45 | 12.13 |
| Colorona Blackstar ® Blue | Black-Blue | 2.25 | 1.62 |
| Colorona Blackstar ® Gold | Black-Gold | 19.38 | 21.19 |
| Colorona Blackstar ® Green | Black-Green | 9.29 | 9.46 |

What is claimed is:

1. A cosmetic composition, comprising a pearlescent pigment,
    wherein the pearlescent pigment is an inorganic material and the color of a homogeneous coating of the pigment, measured over a white background, has a CIELAB L* value of about 30 or less and a chroma value of about 3 or less; and
    wherein the homogeneous coating comprises FeOOH that is partially reduced by a hydrogenation reaction to form a resultant iron oxide, and
    wherein the iron of the resultant iron oxide comprises from about 1% to about 30% Fe(II) and from about 70% to about 99% Fe(III).

2. A cosmetic composition, comprising a pearlescent pigment, wherein the pearlescent pigment is an inorganic material and the color of a homogeneous coating of the pigment, measured over a white background, is selected from the group consisting of:
- a CIELAB hue angle, $h_{ab}$, from about 50 to about 80 degrees, wherein L* is not more than about 85, and the chroma value is greater than 22;
- a CIELAB hue angle, $h_{ab}$, from about 80 to about 275 degrees, wherein L* is not more than about 80, and the chroma value is greater than about 10; and
- a CIELAB hue angle, $h_{ab}$, not less than about 275, or not more than about 50 degrees,
  wherein L* is not more than about 85, and the chroma value is greater than about 9; and
  wherein the homogeneous coating comprises FeOOH that is partially reduced by a hydrogenation reaction to form a resultant iron oxide, and
  wherein the iron of the resultant iron oxide comprises from about 1% to about 30% Fe(II) and from about 70% to about 99% Fe(III).

3. A cosmetic composition, comprising a pearlescent pigment,
wherein the pearlescent pigment is an inorganic material and the color of a homogeneous coating of the pigment is red, pink or violet, with a CIELAB hue angle, $h_{ab}$, not less than about 275, or not more than about 50 degrees, measured over a white background, and wherein the ΔE* of the acid stability for a homogeneous coating of the pigment, measured over a white background, is less than about 4; and
wherein the homogeneous coating comprises FeOOH that is partially reduced by a hydrogenation reaction to form a resultant iron oxide, and
wherein the iron of the resultant iron oxide comprises from about 1% to about 30% Fe(II) and from about 70% to about 99% Fe(III).

4. A cosmetic composition, comprising the pearlescent pigment,
wherein the pearlescent pigment is an inorganic material and the color of a homogeneous coating of the pigment is blue, with a CIELAB hue angle, $h_{ab}$, from about 170 to 275 degrees, measured over a white background; and wherein the ΔE* of the alkaline stability for a homogeneous coating of the pigment, measured over a white background, is less than about 2; and
wherein the homogeneous coating comprises FeOOH that is partially reduced by a hydrogenation reaction to form a resultant iron oxide, and
wherein the iron of the resultant iron oxide comprises from about 1% to about 30% Fe(II) and from about 70% to about 99% Fe(III).

* * * * *